United States Patent
Shank et al.

(10) Patent No.: US 6,231,581 B1
(45) Date of Patent: May 15, 2001

(54) IMPLANTABLE DEVICE ANCHORS

(75) Inventors: Peter J. Shank, Boylston; Kevin R. Heath, Weston; Victor J. Shukhat, West Roxbury; Gary M. Shapiro, Medfield; Makoto Takeuchi, Newton Centre; James E. Windheuser, Hopkinton, all of MA (US)

(73) Assignee: Boston Scientific Corporation, Natick, MA (US)

( * ) Notice: Subject to any disclaimer, the term of this patent is extended or adjusted under 35 U.S.C. 154(b) by 0 days.

(21) Appl. No.: 09/212,760

(22) Filed: Dec. 16, 1998

(51) Int. Cl.[7] .................................................. A61B 17/08

(52) U.S. Cl. ............................................. 606/157; 606/200

(58) Field of Search ................................... 606/200, 151, 606/157, 158, 130, 139, 225; 623/1.1

(56) References Cited

U.S. PATENT DOCUMENTS

| | | | |
|---|---|---|---|
| 3,540,431 | 11/1970 | Mobin-Uddin | 128/1 |
| 3,952,747 | 4/1976 | Kimmell, Jr. | 128/303 R |
| 4,425,908 | 1/1984 | Simon | 128/1 R |
| 4,494,531 | 1/1985 | Gianturco | 128/1 R |
| 4,619,246 | 10/1986 | Molgaard-Nielsen et al. | 128/1 R |
| 4,643,184 | 2/1987 | Mobin-Uddin | 128/303 R |
| 4,688,553 | 8/1987 | Metals | 128/1 R |
| 4,727,873 | 3/1988 | Mobin-Uddin | 128/303 R |
| 4,781,177 | 11/1988 | Lebigot | 128/897 |
| 4,793,348 | 12/1988 | Palmaz | 128/325 |
| 4,817,600 | 4/1989 | Herms et al. | 128/303 R |
| 4,830,003 | 5/1989 | Wolff et al. | 128/343 |
| 4,832,055 | 5/1989 | Palestrant | 128/899 |
| 4,856,516 | 8/1989 | Hillstead | 128/343 |
| 4,943,297 | 7/1990 | Saveliev et al. | 606/200 |
| 4,957,501 | 9/1990 | Lahille et al. | 606/200 |
| 4,969,891 | 11/1990 | Gewertz | 606/200 |
| 4,990,156 | 2/1991 | Lefebvre | 606/200 |
| 5,059,205 | 10/1991 | El-Nounou et al. | 606/200 |
| 5,133,733 | 7/1992 | Rasmussen et al. | 606/200 |
| 5,152,777 | 10/1992 | Goldberg et al. | 606/200 |
| 5,221,261 | 6/1993 | Termin et al. | 604/104 |

(List continued on next page.)

FOREIGN PATENT DOCUMENTS

| | | | |
|---|---|---|---|
| 4030998 A1 | 4/1991 | (DE) | A61F/2/02 |
| 0 348 295 | 12/1989 | (EP) | A61F/2/02 |
| 0 448 891 A1 | 10/1990 | (EP) | A61F/2/02 |
| 0 430 848 A1 | 6/1991 | (EP) | A61F/2/02 |
| 0 462 008 A1 | 12/1991 | (EP) | A61F/2/02 |
| 0 539 237 A1 | 4/1993 | (EP) . | |
| 0 747 020 A2 | 12/1996 | (EP) . | |
| 2 587 901 | 4/1987 | (FR) | A61M/1/34 |
| 2 649 884 | 1/1991 | (FR) | A61B/17/00 |
| 2713 915 | 6/1995 | (FR) . | |
| 2 200 848 | 8/1988 | (GB) | A61F/2/00 |
| 835447 | 6/1981 | (RU) | A61M/1/03 |
| WO 91/04716 | 4/1991 | (WO) | A61F/2/02 |
| WO 91/11972 | 8/1991 | (WO) | A61F/2/06 |
| WO 95/09567 | 4/1995 | (WO) . | |
| WO 96/17634 | 6/1996 | (WO) | A61B/17/00 |
| WO 97/28745 | 8/1997 | (WO) . | |

OTHER PUBLICATIONS

Annals of Vascular Surgery, Int'l Journal of Vascular Surgery, Mar. 1992, vol. 6, #2, Detroit, "Conical Endocaval Filters with Metallic Struts; Search for a New Model," Kraimps et al.

"Optimal Central Trapping (OPCETRA) Vena Caval Filter: Results of Experimental Studies" Kraimps, et al. JVIR 1992: 3:697–701.

*Primary Examiner*—Kevin Truong
(74) *Attorney, Agent, or Firm*—Hoffmann & Baron, LLP

(57) ABSTRACT

An anchor secures an implantable device within a body by engaging a wall of the body. The anchor includes a shank and an arm extending from the shank. The shank and the arm are integrally formed from a single member. The shank attaches to the device.

47 Claims, 31 Drawing Sheets

U.S. PATENT DOCUMENTS

| | | |
|---|---|---|
| 5,108,418 | 4/1992 | Lefebvre . |
| 5,300,086 | 4/1994 | Gory et al. .......................... 606/200 |
| 5,304,200 | 4/1994 | Spaulding .......................... 606/198 |
| 5,324,304 | 6/1994 | Rasmussen .......................... 606/200 |
| 5,344,427 * | 9/1994 | Cottenceau et al. ................ 606/200 |
| 5,370,657 | 12/1994 | Irie .................................... 606/200 |
| 5,375,612 | 12/1994 | Cottenceau et al. ................ 128/899 |
| 5,522,822 | 6/1996 | Phelps et al. ....................... 606/151 |
| 5,549,626 | 8/1996 | Miller et al. ....................... 606/200 |
| 5,601,595 | 2/1997 | Smith .................................. 606/200 |
| 5,630,829 | 5/1997 | Leuterjung . |
| 5,634,942 | 6/1997 | Chevillon et al. ..................... 623/1 |
| 5,683,411 | 11/1997 | Kavteladze et al. ................ 606/200 |
| 5,709,704 | 1/1998 | Nott et al. .......................... 606/200 |
| 5,725,550 * | 3/1998 | Nadal .................................. 606/200 |
| 5,836,969 | 11/1998 | Kim et al. .......................... 606/200 |
| 5,891,160 | 4/1999 | Williamson, IV et al. . |
| 5,916,224 * | 6/1999 | Esplin ................................. 606/151 |

* cited by examiner

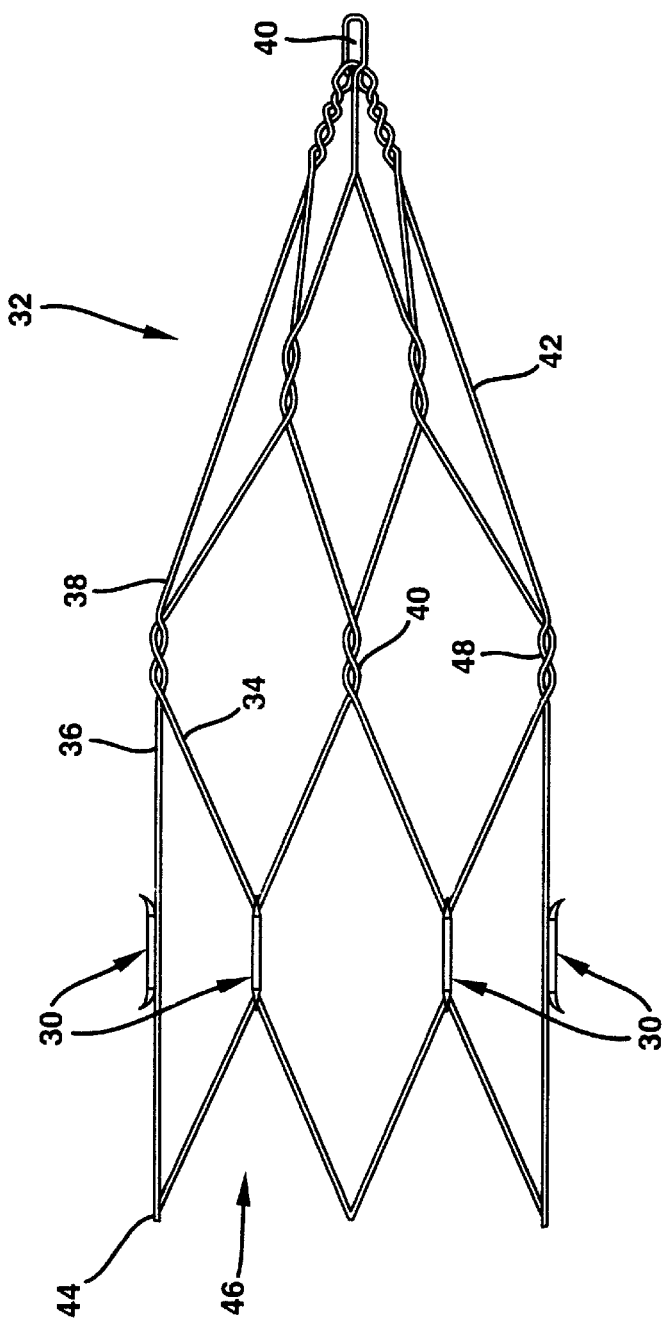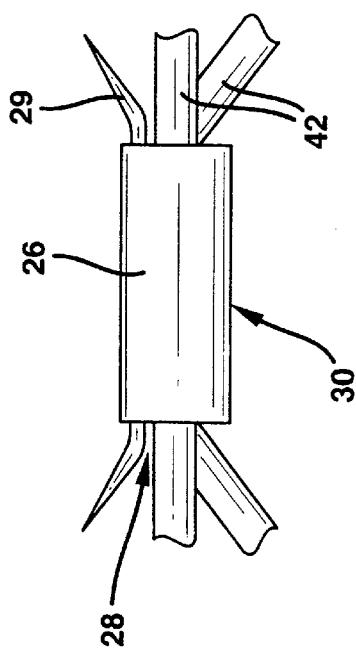
FIG. 2 PRIOR ART
FIG. 3 PRIOR ART

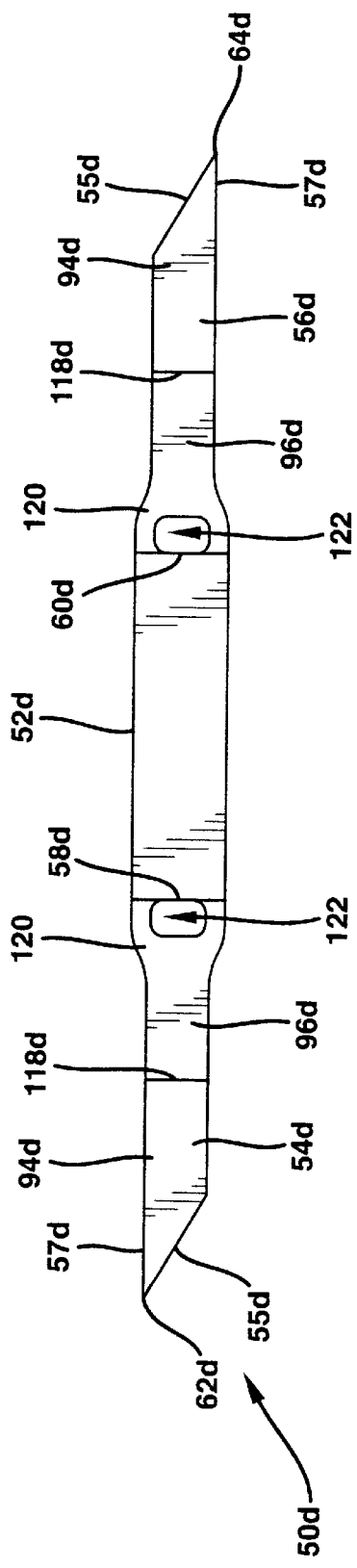

IMPLANTABLE DEVICE ANCHORS

BACKGROUND OF THE INVENTION

The invention relates to implantable devices, and, in particular, to anchors that secure implantable medical devices.

Implantable medical devices, such as blood filters, stents, and grafts, are deployed within a body, for example, in a blood vessel, during both surgical and non-surgical medical procedures. An anchor secures the device in place by either piercing or pressing outwardly against the wall of the blood vessel. A physician compresses the medical device and inserts the device into the blood vessel. When the device expands, the anchor engages the wall of the blood vessel to secure the implantable medical device. In addition, other types of medical devices require anchoring within the body generally, such as valves, pacing leads, tethered devices that are removable, embolic devices, and infusion devices. A physician places such devices in, for example, blood vessels, intestines, other lumens, and other portions of the body.

For example, referring to FIG. 1, a prior art blood filter 10 resides within a lumen, for example, a blood vessel 12. Filter 10 prevents clots in the blood from flowing within blood vessel 12 to other areas of the body located downstream of filter, especially the heart, lungs, and brain. Filter 10 is generally conical and has a set of six corrugated (or zig-zagged) arms 16 that extend from an apical end 17. Arms 16 act in conjunction with each other to filter clots from the blood. Typically, filter 10 is compressed within a delivery sleeve (not shown) at the end of a catheter. A physician inserts the compressed filter 10 into a lumen such as blood vessel 12. Once filter 10 is inside blood vessel 12, the physician removes the delivery sleeve, and filter 10 expands. Arms 16 exert a radial force transverse to a central axis 24 of the filter 10 against a wall 22 of vessel 12.

Each arm 16 has a corresponding end 18 that forms one of six hooks 14a–14f. When filter 10 expands into the position shown in FIG. 1, hooks 14a–14f engage with wall 22, preventing filter 10 from migrating within blood vessel 12, for example, the vena cava. Each hook 14a–14f terminates at a corresponding point 20. The radial force of arms 16 causes points 20 to pierce wall 22. Hooks 14a, 14c, 14d, and 14f each have a corresponding point 20 oriented in the direction of blood flow. Thus, hooks 14a, 14c, 14d, and 14f counteract the force of the blood rushing through filter 10 and prevent the migration of filter 10 within blood vessel 12. In addition, hooks 14b and 14e each have corresponding points 20 that are oriented in the direction opposite the blood-flow. Thus, hooks 14b and 14e prevent migration of filter in the direction opposite the blood flow, which may be caused, for example, by movement of the body.

Referring to FIGS. 2 and 3, another type of prior art blood clot filter 32 includes a wire mesh 34. Wire mesh 34 has a cylindrical portion 36 and a conical portion 38. Conical portion 38 extends from an apical end 40. An opposite end 44 of filter 32 includes an opening 46 that allows blood and clots to flow into filter 32. Filter 32 is described in greater detail in U.S. patent application Ser. No. 09/008,258, the entire disclosure of which is incorporated herein by reference.

Filter 32 also includes anchors 30. Anchors 30 include two separate pieces: a shank 26, which defines a hollow 28, and a hook 29, which is a metallic strip centered within hollow 28. Anchors 30 attach to wire strands 42 at junctures 48 where wire strands 42 intersect. Hook 29, and two wire strands 42, extend through hollow 28. Shank 26, hook 29, and wire strands 42 are welded together.

An implantable medical device, such as filter 10 or filter 32, typically must be compressible to a diameter smaller than the diameter of the body lumen in which it is to be implanted. The compressed diameter of the device thus limits its use. Anchoring devices, such as hooks 14a–14f or anchors 30, have profiles that limit the contraction of a blood filter or other medical device.

SUMMARY OF THE INVENTION

In one aspect, the invention provides a low profile anchor adapted to secure an implantable device within a body by engaging the wall of the body. The anchor includes a shank and at least one arm that extends from the shank. The shank and the arm are integrally formed from a single member. The shank is adapted for attachment to a device, and the first arm is adapted for engaging the wall of the body when the device is implanted within a body.

Embodiments of this aspect of the invention may include one or more of the following features. The anchor has two arms, and each arm extends from a corresponding opposite end of the shank. The arms extend in opposing directions relative to a longitudinal axis.

The shank and the arms are integrally formed from flat stock. The shank may be an elongated section disposed at an angle to both the first arm and the second arm. At least a portion of the shank is curled about the axis to form a loop. Alternatively, the shank may have several different embodiments. The shank may be a single strip curled about the axis to form a plurality of loops that are adjacent to one another. The shank may be curled about the axis until one edge of the shank is oriented in substantially the same direction as an opposite edge of the shank. The shank may include tab sections that extend from opposite edges of the shank and that are curled about the axis. The shank may extend along the axis at an angle to two arms, which are respective openings aligned along the axis, and the shank may include a slot that extends between and connects the openings. The shank may be a hollow tube with a cylindrical shape, elliptical shape, or a pair of lobes.

Similarly, the arms may have several different embodiments. The arms of the anchor may extend at an angle relative to the axis or may parallel the axis. The arms may be curved. The arms may include one or more bends. The arms may include a pointed end, a rounded end, or a flat end. The arms may include sharp or dull edges. The arms may be resilient.

The anchor may be constructed of shape memory material, stainless steel, or titanium. The anchor may be attached to an implantable device, such as blood clot filters, grafts, stents, valves, pacing leads, tethered devices that are removable, embolic devices, and infusion devices.

In another aspect, the invention provides a process for making an anchor for securing an implantable device in a body. The process includes the steps of forming flat stock into a member having a shank section and at least one arm section, and bending the shank section about an axis. The process may additionally include configuring the arm sections by shaping, angling, curving, bending, twisting, sharpening, or dulling the arm sections.

In still another aspect, the invention provides a process for making an anchor for securing an implantable device in a body. The process includes the steps of forming a member into a shape having a shank section and at least one arm section, and providing a hollow within the shank section. The process may additionally include configuring the arm sections by shaping, angling, curving, bending, twisting, sharpening, or dulling the arm sections.

Embodiments of the invention may have one or more of the following advantages. Anchors according to the invention allow an implantable device, such as a blood clot filter, to be compressed to a relatively small profile and be inserted into a relatively small lumen. The anchor may be small relative to the lumen or the implantable device. The anchor is formed from a single piece of material. The anchor can be produced efficiently. The arms of the anchor may be resilient. The arms may contract to reduce the profile of the anchor during insertion. The arms may expand to engage the walls of a lumen. An anchor configured with a single arm can provide a preferred engagement within a body, especially within a body lumen. The anchor may have a variety of configurations to accommodate different surgical applications and procedures. The anchor easily attaches to an implantable device. The anchor is compatible with a variety of implantable devices.

BRIEF DESCRIPTION OF THE DRAWINGS

FIG. 2 is a schematic view of a filter having anchors according to the invention;

FIG. 3 is a close-up schematic view of the anchor encircled in FIG. 2;

FIG. 17 is a top view of another anchor according to the invention;

FIG. 18 is a side view of the anchor of FIG. 17;

DESCRIPTION OF THE PREFERRED EMBODIMENTS

Figure 4:
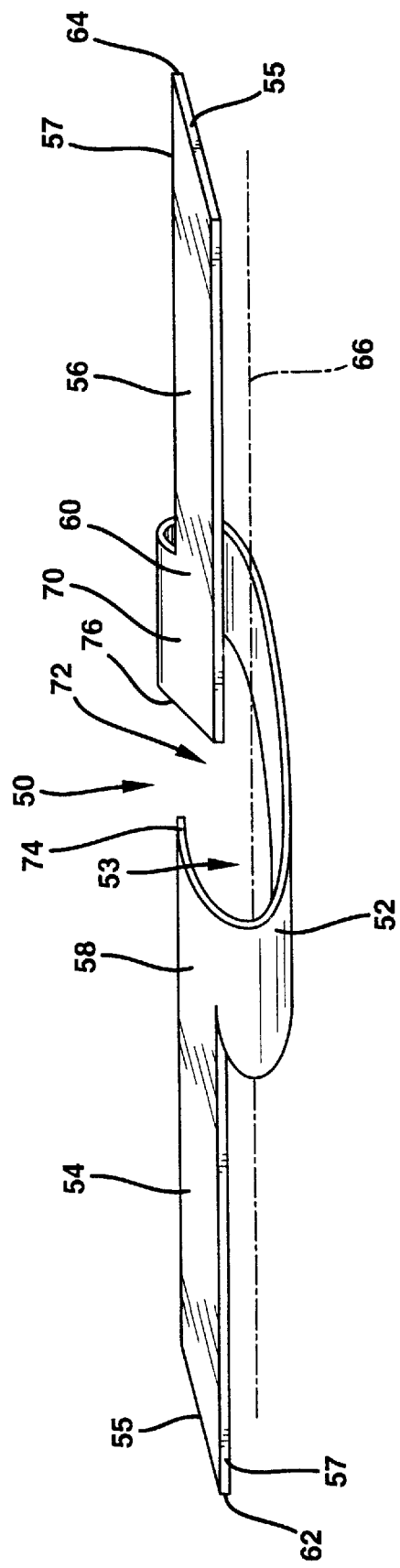
FIG. 4 is a perspective view of one embodiment of an anchor according to the invention.

Referring to FIG. 4, anchor 50 includes a shank 52 and two arms 54, 56 extending in opposite directions from corresponding ends of shank 52. Shank 52 curves about a longitudinal axis 66, and forms a central passage 53. Each of arms 54, 56 includes two side edges 55, 57 near respective ends 62, 64. Side edges 55, 57 intersect at a 40 degree angle ±15 degrees, which forms a sharp point at each corresponding end 62, 64. Anchor 50 is symmetrical along axis 66 and, thus, has the same relative appearance when viewed from either end 62, 64, as also shown in FIG. 5.

Figure 5:
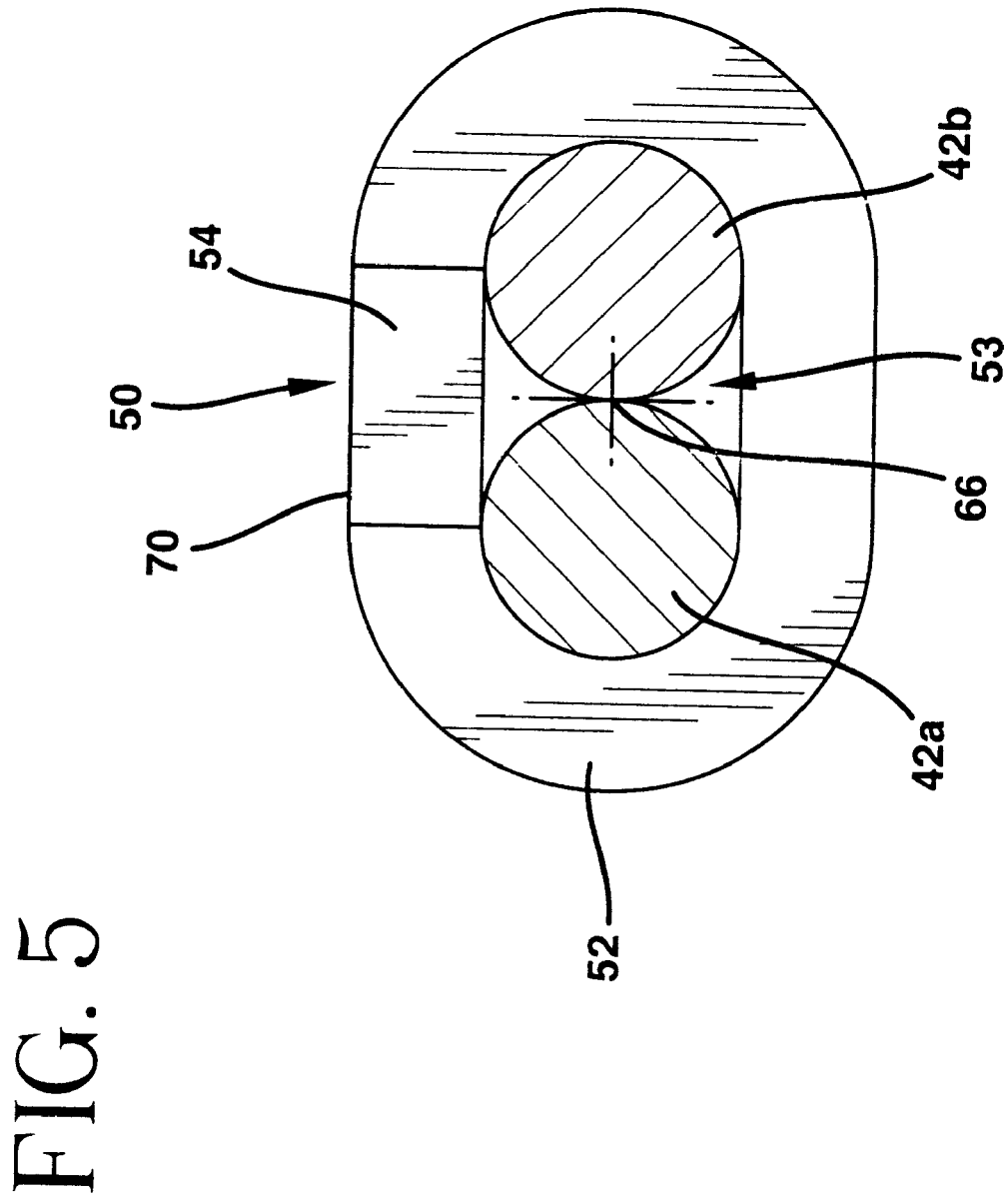
FIG. 5 is an end view of the anchor of FIG. 4 attached to two wires of a surgical implant, which are shown in cross-section.

Referring also to FIG. 5, anchor 50 is attached to an implantable medical device according to the following procedure. One or more wire segments of a medical device, such as two wire segments 42a and 42b of filter 32, are passed through central passage 53 along axis 66. Passage 53 has an ovular shape, and shank 52 fits closely around wires 42a, 42b such that the inner wall of shank 52 contacts close to half of the outer circumference of each wire 42a, 42b. Shank 52 holds wires 42a, 42b together within passage 53, and wires 42a, 42b touch along axis 66. Anchor 50 is positioned along wires 42a, 42b such that arms 54, 56 extend above wires 42a, 42b on the outer periphery of the medical device, for example, blood clot filter 32 as shown in FIG. 2. Once positioned, wires 42a, 42b are laser welded to shank 52 along a top section 70 of shank 52. The process of laser welding depends on several factors including the materials of the anchor 50 and the medical device, the surface area of the materials, the volume of the materials, and the size of the tooling (larger tooling acts as a heat sink and requires more energy).

For example, to laser weld a typical embodiment of anchor 50, the laser beam spot size at the point of welding is 0.010"±0.002" for a duration of 2 ms±10–20% with an energy of 1.22 Joules ±0.1 Joules. Alternatively, wires 42a, 42b and shank 52 can be resistance welded under an inert gas shield with approximately 70 ounces of force and 10 Joules of heat.

Figure 6:
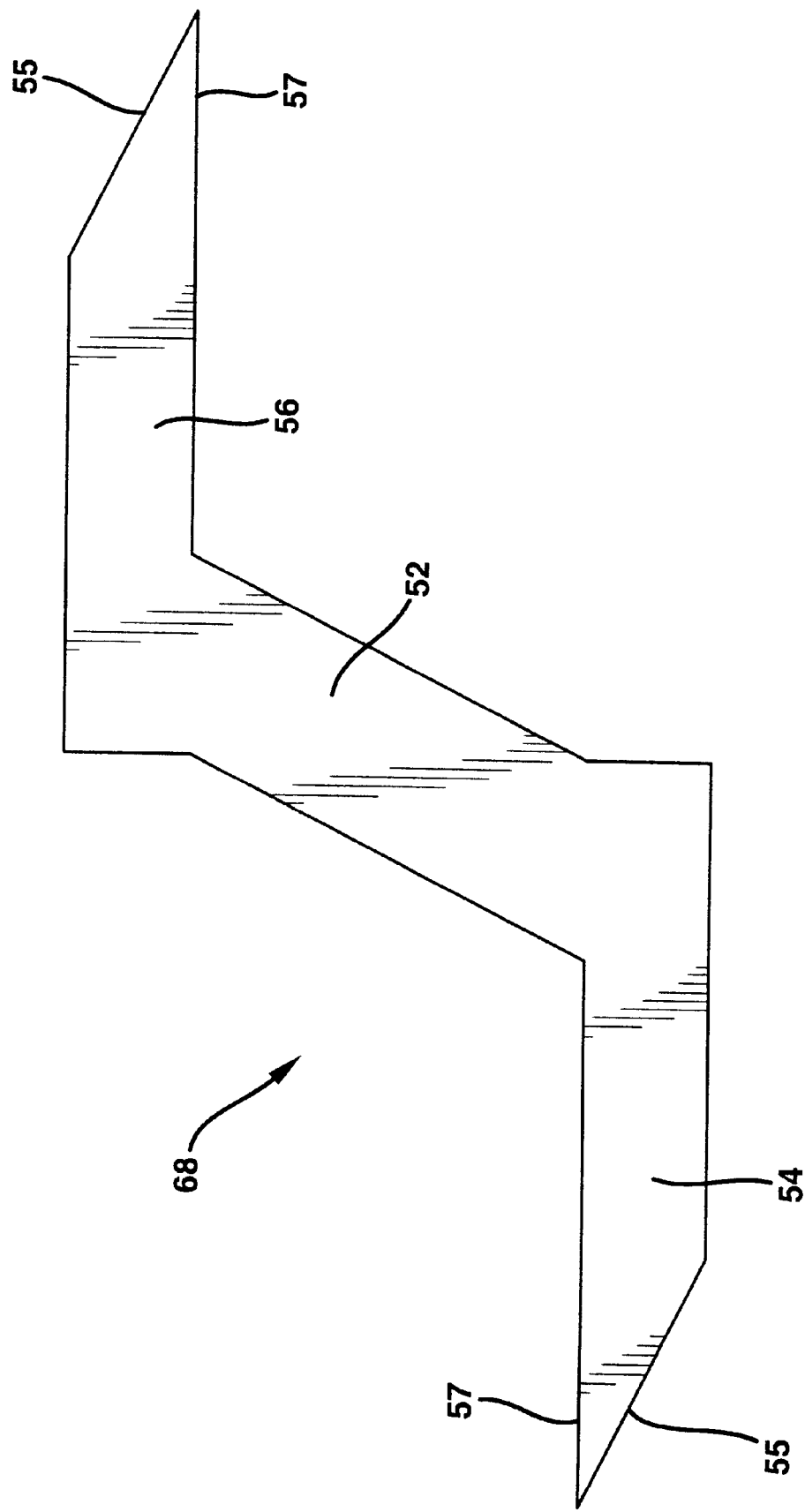
FIG. 6 is a plan view of a section of flat stock used to form the anchor of FIGS. 4 and 5.

Referring now to FIG. 6, anchor 50 is formed from a single member 68. Member 68 has a planar shape that is cut from a section of flat stock. Member 68 is cut by using a pre-shaped press that moves normally to the plane of the flat stock material. The flat stock material can be titanium, stainless steel, shape memory material, such as Nitinol, or any other surgically implantable material that can be cut, shaped, and affixed as described herein. The flat stock material is, for example, 0.005"±0.0005" in thickness. When member 68 is flat, arms 54, 56 extend in parallel. Shank 52 extends transversely between arms, and lies at an angle relative to arms 54, 56.

To form anchor 50, shank 52 is curled into a helical loop about axis 66, and arms 54, 56 are aligned parallel with axis 66. A top section 70 is flat, as shown in FIG. 5, and, thus, arms 54, 56 are flat. When shank 52 is curled about axis 66, a space 72 exists between proximal ends 74, 76 of respective arms 54, 56. Alternatively, the member can be structured to be curled with a tighter pitch such that proximal ends 74, 76 are directly adjacent, which eliminates space 72.

Figure 7A:
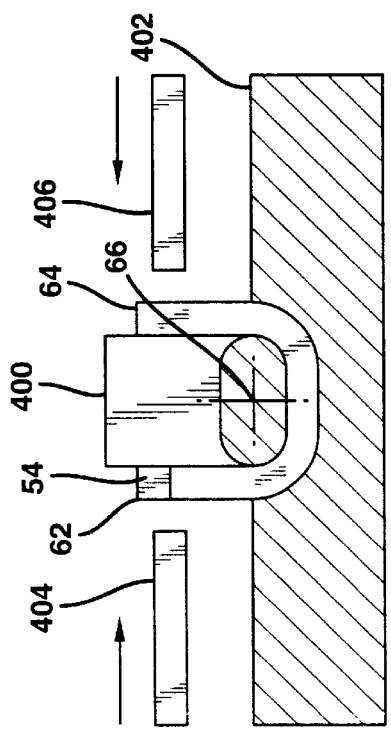
FIGS. 7a–7b are schematic views of a set of tools used to form the anchor of FIG. 4 in a vertical direction.
Figure 8A:
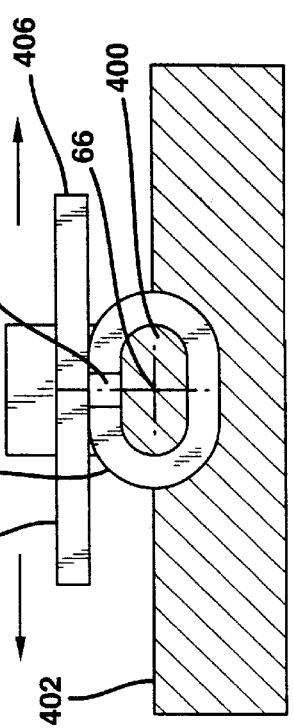
FIGS. 8a–8b are schematic views of a set of tools used to form the anchor of FIG. 4 in a horizontal direction.
Figure 7B:
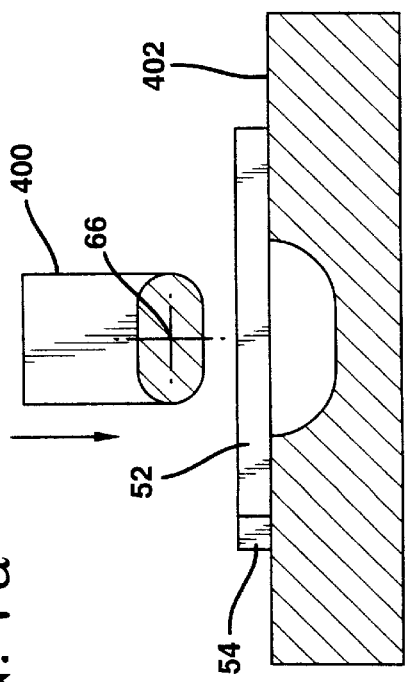
Figure 8B:
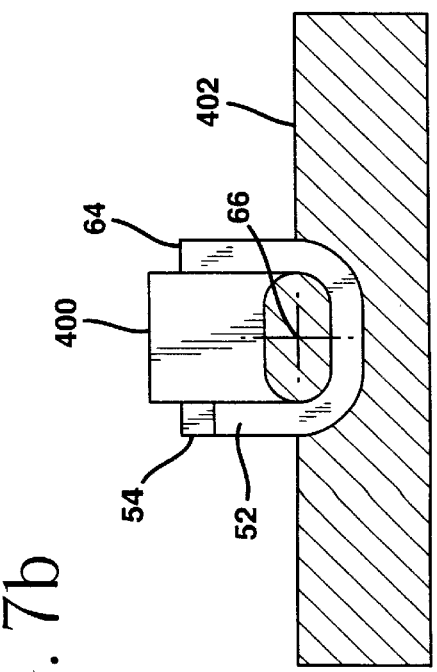

A four step process is used to form anchor 50. First, the manufacturer selects the appropriate flat stock material and cuts the material into single member 68 having a shank section and two arm sections. Second, referring to FIGS. 7a–7b, a curved, "U"-shaped knife edge 400 (one half of the "U" being shown in cross-section) presses shank 52 against a form 402. Third, referring to FIGS. 8a–8b, after removing knife edge 400, two horizontal knife edges 404, 406, which also have lengths that parallel axis 66, fold opposite ends 62, 64 of arms 54, 56 together about the bottom portion of the "U"-shaped knife edge 400. The bottom portion of knife edge 400 has a shape that corresponds with the desired shape of the passage. However, knife edge 400 accounts for the resiliency of the material used to form the anchor because metals used to form anchors according to the invention tend to spring back to a degree when knife edges 404, 406 are removed.

Finally, after shank 52 is curled about axis 66, the manufacturer can configure arms 54, 56. Arms 54, 56 can be oriented as illustrated in FIGS. 4–6 without further manipulation of anchor 50. Also, as with all embodiments described in this specification, the manufacturer can configure arms 54, 56 in an alternate manner to accommodate a specific application, such as deployment in a vein or an artery as discussed below.

Figure 1:
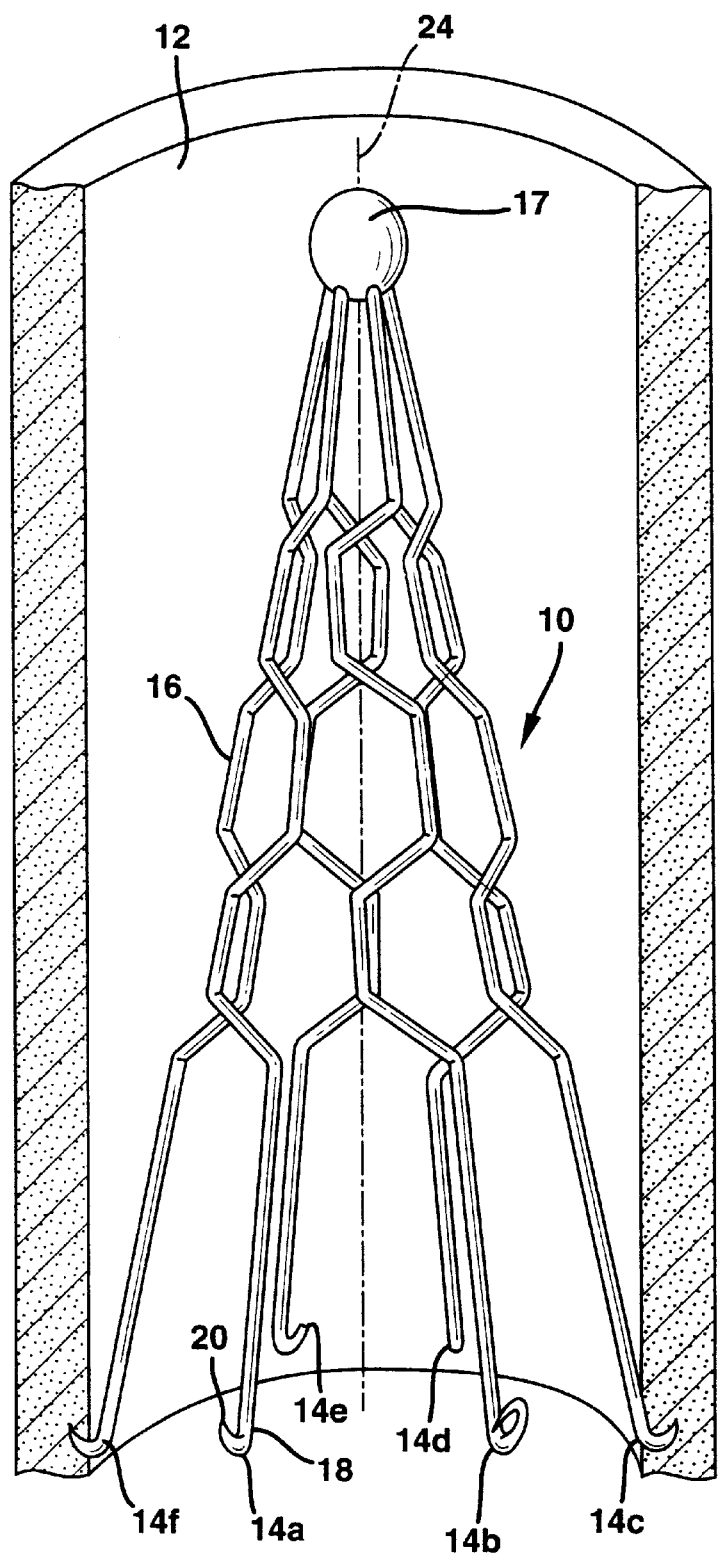
FIG. 1 is a partial cross-sectional view of a lumen containing a filter known in the prior art.

In operation, anchor 50 secures an implantable medical device, such as filter 32, a graft, or a stent, within a lumen, such as blood vessel 12 shown in FIG. 1. The arms 54, 56 of the anchor 50 secure the implantable medical device. In the embodiment shown in FIG. 4, arms 54, 56 engage wall 22 of blood vessel 12. Arms 54, 56 have pointed ends that pierce wall 22 of lumen 12. However, other arm configurations are possible as described in the embodiments below.

Different arm configurations facilitate different applications of the implantable medical device. For example, a vein, when compared to an artery, is more elastic, is less muscular, and may heal more readily if punctured (e.g., when the arm of the anchor extends through the entire thickness of the wall of the lumen). To accommodate the physical differences between arteries and veins, the arms of an anchor deployed in a vein may be configured to bow toward the wall of the lumen to a greater extent than the arms of an anchor deployed in an artery. For example, a distal portion of each arm of the anchor deployed in the vein may diverge away from the longitudinal axis at a greater angle than the arms of the anchor deployed in the artery. In addition, each arm of the anchor deployed in a vein may have a relatively sharper distal end than the arms of the anchor deployed in the artery.

The arms of the anchor deployed in the artery may be less traumatic than the arms of the anchor deployed in the vein to reduce the risk of damaging the artery. A less traumatic anchor is less likely to pierce and damage a lumen. Therefore, arms of the anchor deployed in the artery may be flat with dull ends, or may be configured to shallowly pierce the wall of the artery.

For most arm configurations, the shank of the anchor prevents the arms from extending through the wall of the blood vessel. The shank abuts the inner wall of the blood vessel and prevents further advancement of the arms through the wall of the blood vessel.

The following examples describe other embodiments of the invention.

Figure 9:
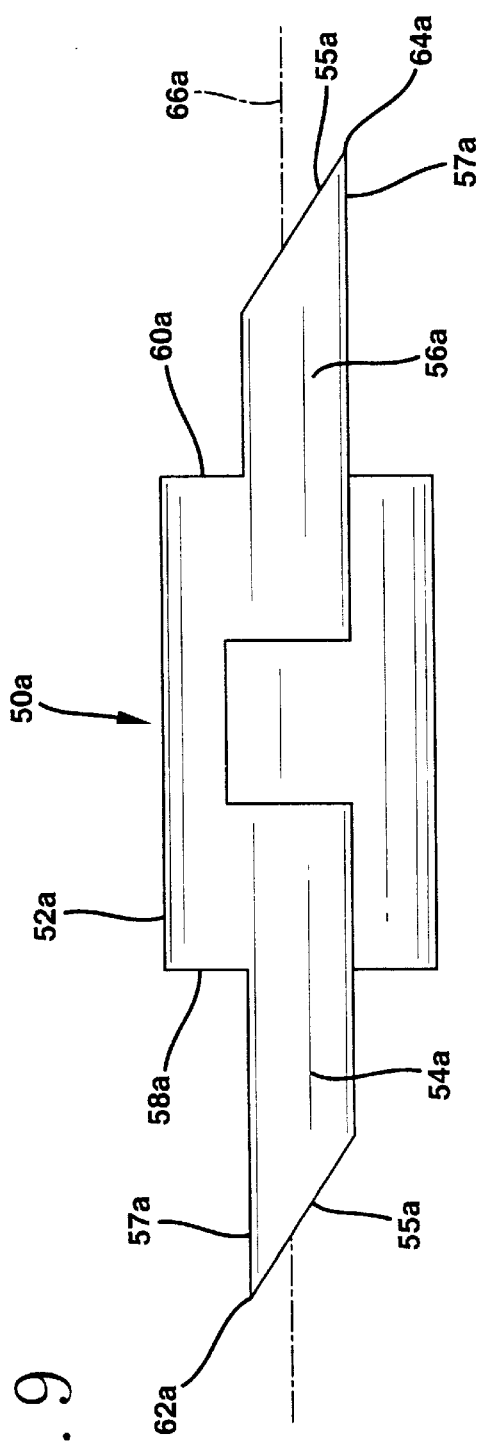
FIG. 9 is a top view of another embodiment of the invention.
Figure 10:
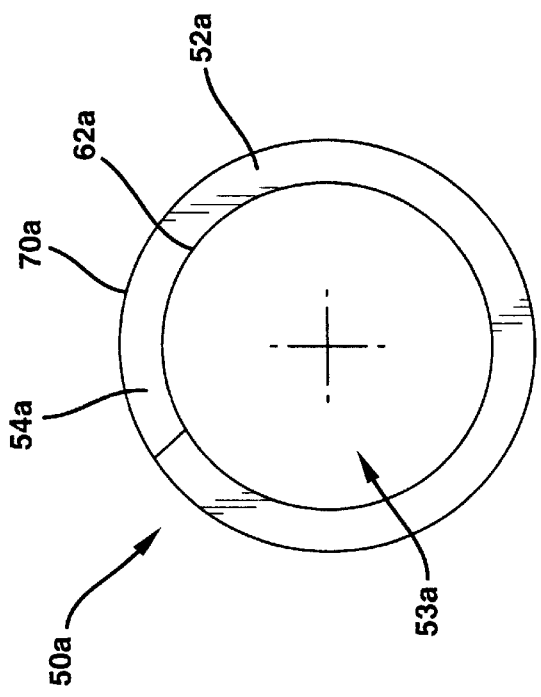
FIG. 10 is an end view of the anchor of FIG. 9.

Referring to FIGS. 9–10, anchor 50a includes a shank 52a and two arms 54a, 56a extending from corresponding opposite ends 58a, 60a, respectively, of shank 52a. Shank 52a curves about a longitudinal axis 66a, and forms a central passage 53a. Each arm 54a, 56a includes two side edges 55a, 57a near respective ends 62a, 64a. Side edges 55a, 57a intersect at a 40 degree angle ±15 degrees, which forms a sharp point at each corresponding end 62a, 64a. Anchor 50a is symmetrical along axis 66a and, thus, has the same relative appearance when viewed from either end 62a, 64a.

In contrast to flat top section 70 of anchor 50 illustrated in FIG. 5, top section 70a curves, and, thus, arms 54a, 56a are curved along the width of each arm 54a, 56a, i.e., arms 54a, 56a are curved in a direction that is transverse to axis 66a. However, similar to arms 54, 56 of anchor 50, arms 54a, 56a of anchor 50a are flat in a direction that is parallel to axis 66a.

Figure 11:
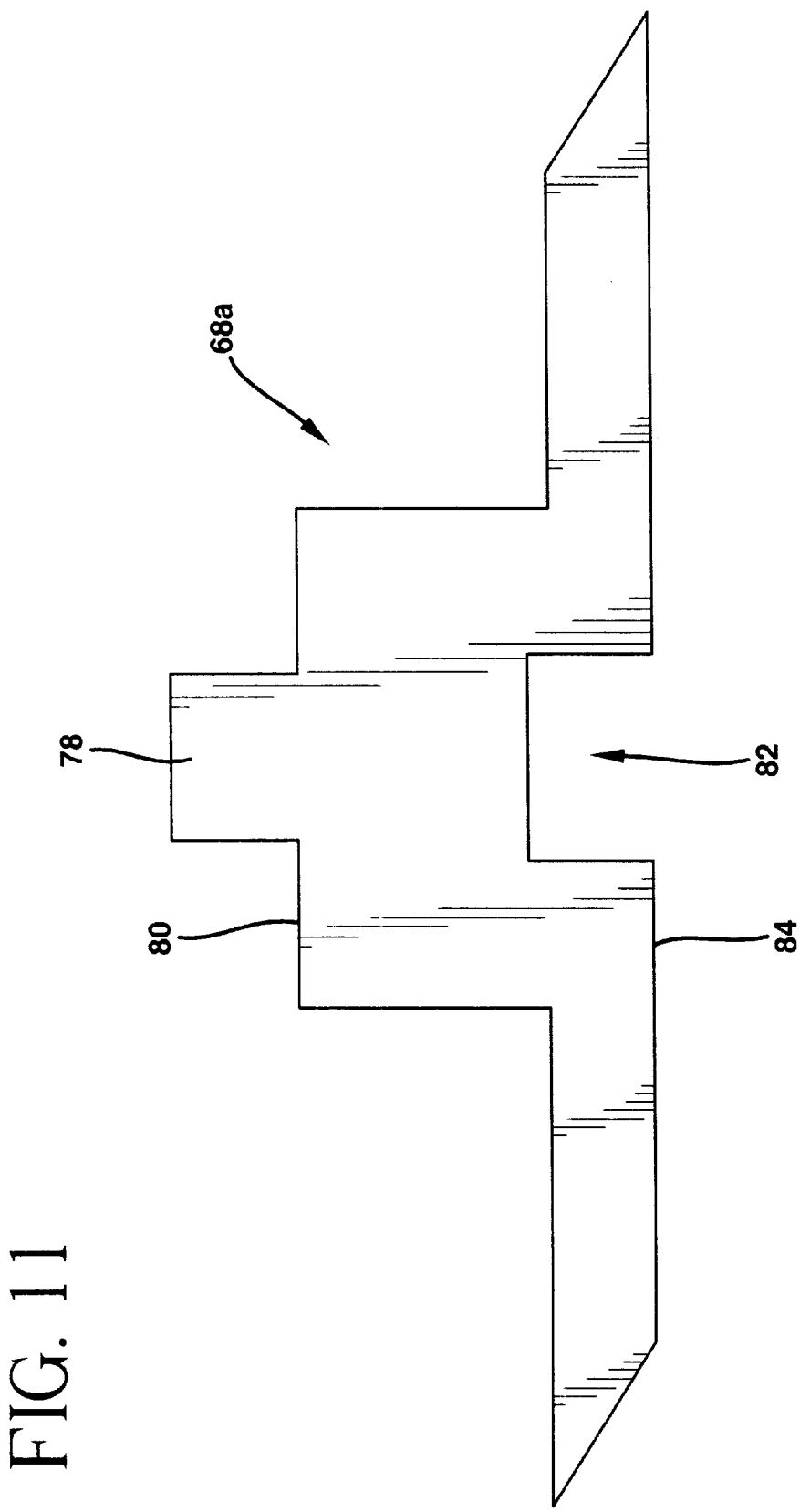
FIG. 11 is a plan view of a section of flat stock used to form the anchor of FIG. 9.

Referring to FIG. 11, a planar member 68a, which is cut from flat stock material, forms anchor 50a. Member 68a includes a tab 78 on one side 80, and a notch 82 on opposing side 84. Tab 78 and notch 82 are aligned in a direction transverse to axis 66. Tab 78 is the same shape, and has the same dimensions, as notch 82.

Anchor 50a is formed in a manner similar to anchor 50. When member 68a is curled about axis 66a, side 80 of anchor 50a is directly adjacent to, and abuts, side 84, and tab 78 resides within notch 82. Abutting sides 80, 84 form a seam along the length of shank 52a when anchor 50a is fully formed.

Figure 12:
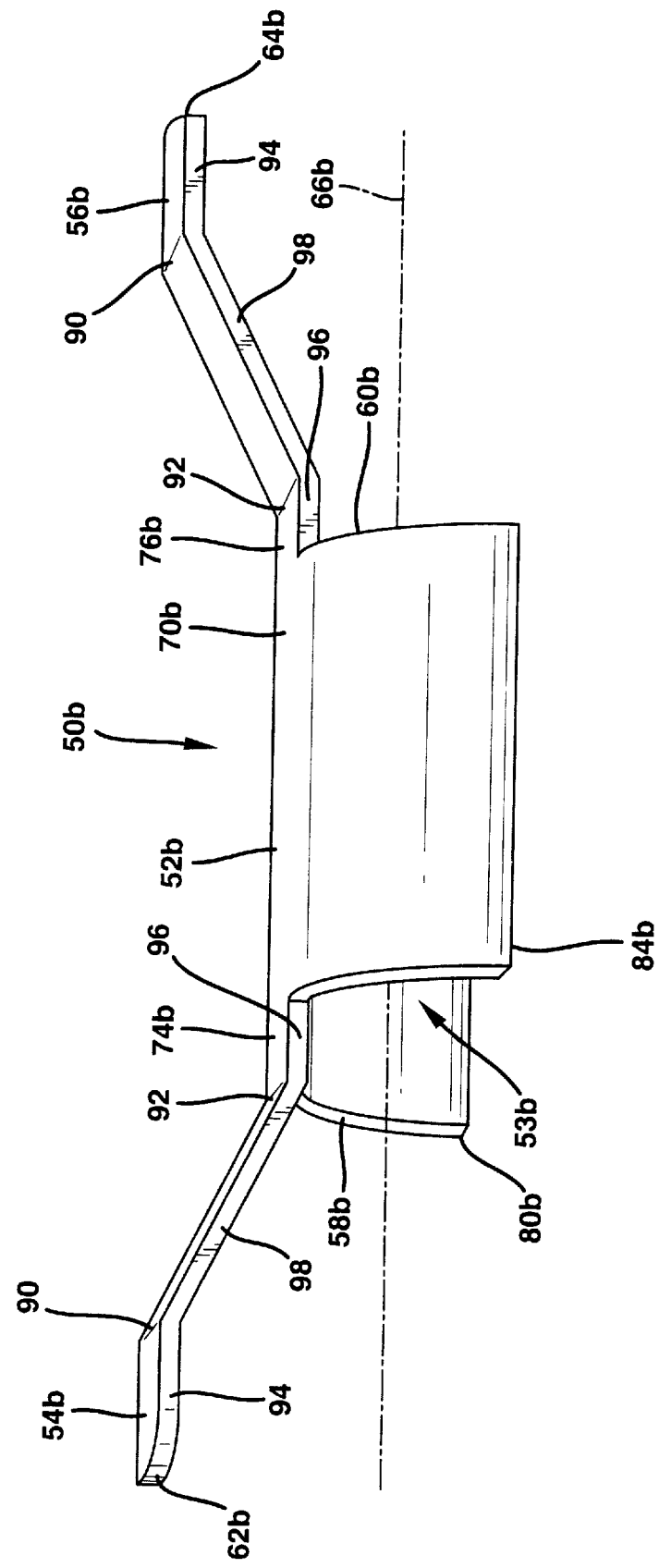
FIG. 12 is a perspective view of a different embodiment of the invention.

Referring to FIG. 12, anchor 50b includes a shank 52b and two arms 54b, 56b. Shank 52b extends between arms 54b, 56b. Shank 52b curves about a longitudinal axis 66b, and forms a passage 53b, which is approximately semicircular. The semicircular curve orients two sides 80b, 84b of shank 52b downward such that they are substantially parallel. Proximal ends 74b, 76b of respective arms 54b, 56b have approximately the same curvature as shank 52b. However, arms 54b, 56b flatten as arms 54b, 56b extend away from shank 52b.

Arms 54b, 56b extend in opposite directions relative to axis 66b from the middle of corresponding ends 58b, 60b of shank 52b. Arms 54b, 56b each include two bends 90, 92 that divide each arm 54b, 56b into three sections: a distal section 94, a proximal section 96, and a central section 98. Distal and proximal sections 94, 96 are parallel to each other, and, relative to proximal section 96, distal section 94 is elevated transversely away from axis 66b. Central section 98 connects distal and proximal sections 92, 94. Distal section 94 of each arm 54b, 56b includes a corresponding end 62b, 64b. Each end 62b, 64b is rounded across the width of each corresponding arm 54b, 56b.

Bends 90, 92 allow arms 54b, 56b to properly engage the wall of a blood vessel. In addition, bends 90, 92 of each arm 54b, 56b prevent corresponding distal ends 62b, 64b of the arms 54b, 56b from engaging the wall of a catheter used to implant the medical device. As resilient arms 54b, 56b flatten within the catheter, corresponding ends 62b, 64b rotate downward and face away from the wall of the catheter. When in the catheter, ends 62b, 64b point toward axis 66b.

Different anchors can have different configurations. For example, like anchor 50a (FIG. 10), anchor 50b (FIG. 12) can be configured to fully encompass one or more wires. In such a configuration, the width of shank 52b may be adjusted to fit a particular number or size of wire(s) or other structure. When compared to the configuration of anchor 50b illustrated in FIG. 10, such an alternative configuration may require additional manufacturing steps and may decrease the access to the wires during welding. However, such an alternative configuration may provide additional structural support and strain relief which could be beneficial in certain applications where the implantable device may experience relatively greater stresses.

Figure 13:
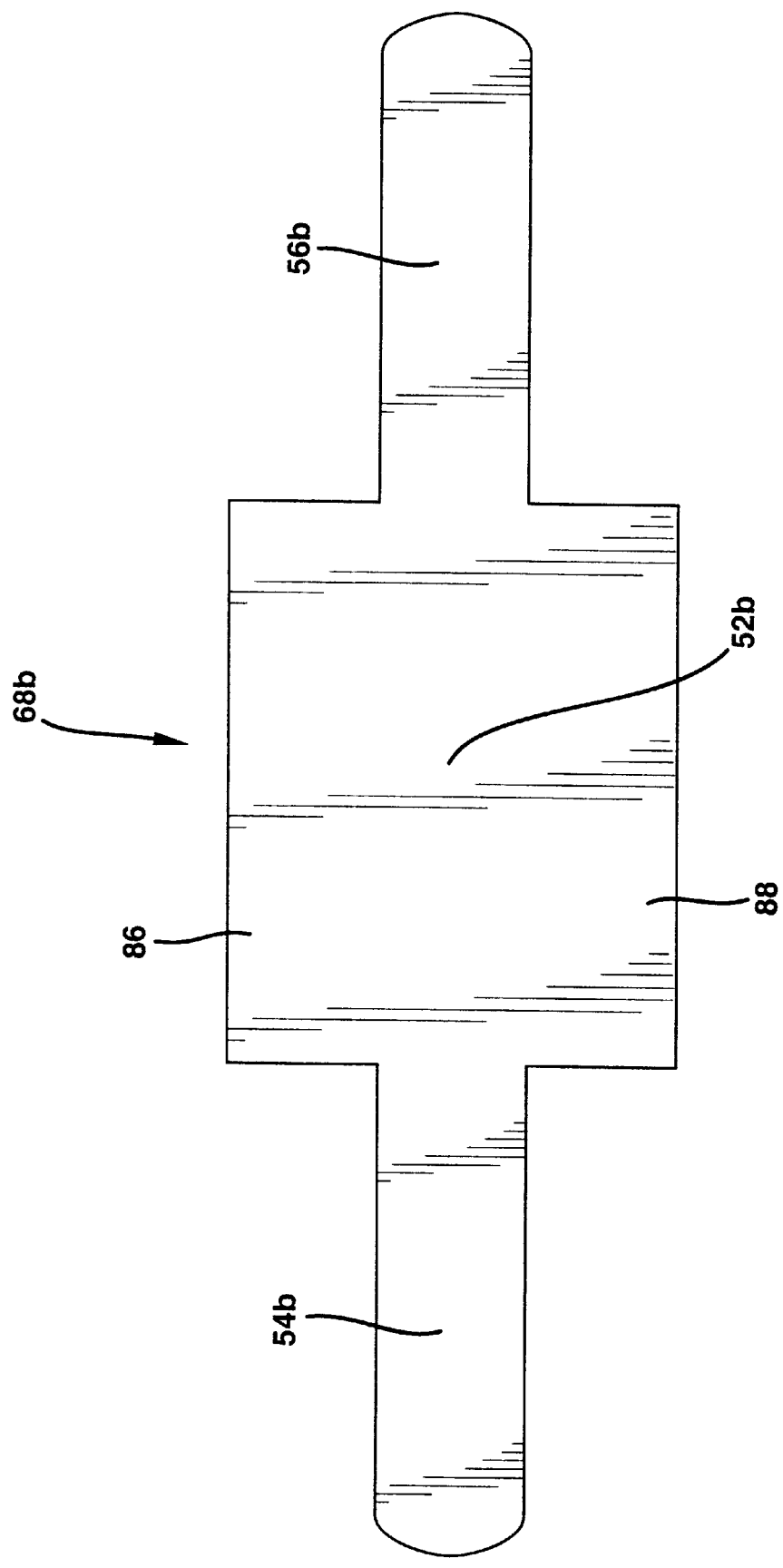
FIG. 13 is a plan view of a section of flat stock used to form the anchor FIG. 12.

Referring to FIG. 13, a planar member 68b, which is cut from flat stock material, forms anchor 50b. Member 68b includes two tabs 86, 88 that form the semicircular curve of shank 52b. When member 68b is flat, shank 52b has a rectangular shape that has a length along axis 66b and a width that is transverse to axis 66b. Anchor 50b is formed in a manner similar to anchor 50. However, member 68b is only partially curled about axis 66b to form the semicircular curve. The second step, wherein the knife edges press sides 80b, 84b together, is not employed. Anchor 50b is easier to form than anchor 50. However, a device using anchor 50b, e.g., a filter in combination with anchor 50b, may not be as strong or fatigue resistant as a device using anchor 50.

Figure 14:
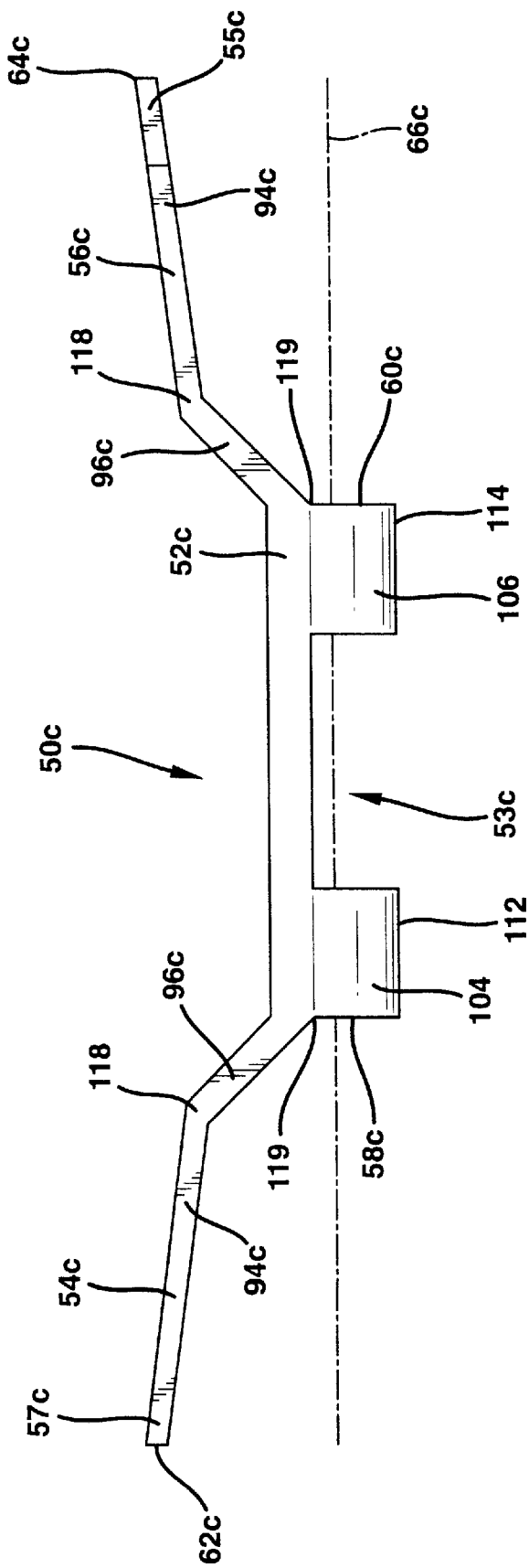
FIG. 14 is a perspective view of a further embodiment of the invention.
Figure 15:
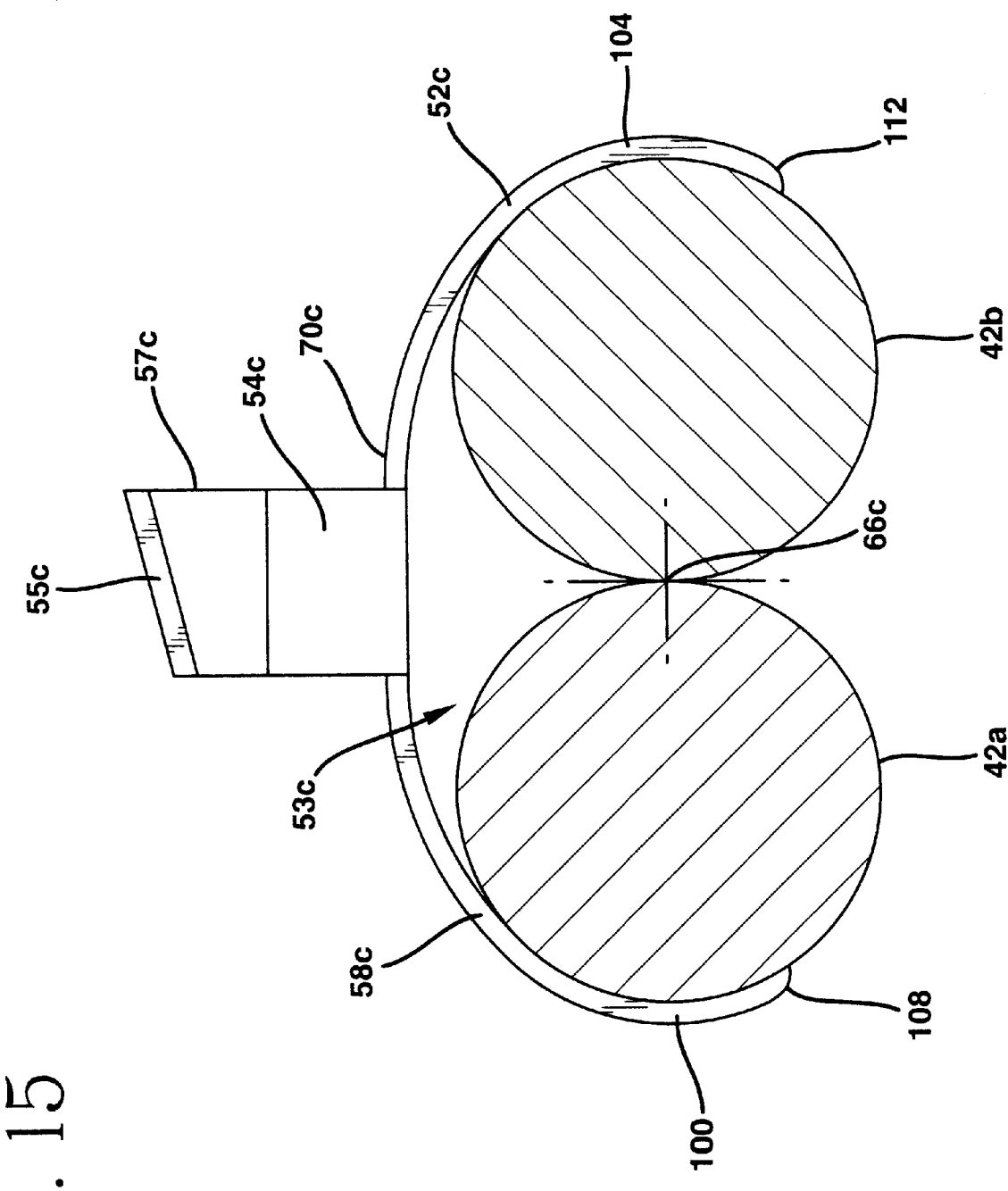
FIG. 15 is an end view of the anchor of FIG. 14 that is attached to two wires of a surgical implant, which are shown in cross-section.
Figure 16:
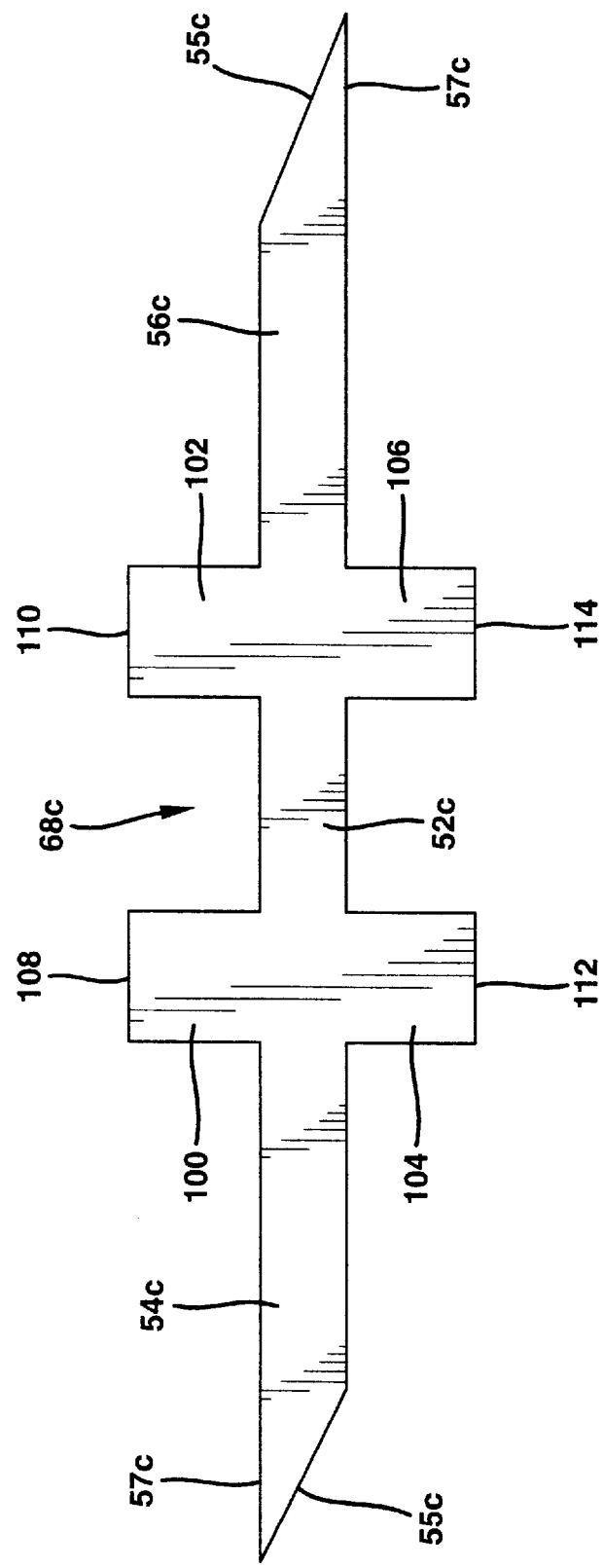
FIG. 16 is a plan view of a section of flat stock used to form the anchor of FIG. 14.

Referring to FIGS. 14–16, anchor 50c includes a shank 52c and two arms 54c, 56c. Shank 52c extends between arms 54c, 56c. Shank 52c includes four tabs 100, 102, 104, 106. Tabs 100, 102 are positioned opposite tabs 104, 106, respectively, in a direction that is transverse to a longitudinal axis 66c. The opposing pairs of tabs 100, 104 and 102, 106 curve about a longitudinal axis 66c to form two similar arcs. Curved tabs 100, 102, 104, 106 form an open passage 53c.

Unlike the semicircular curve of shank 52b, shown in FIG. 13, which extends 180 degrees, the arcs of shank 52c extend further than 180 degrees. Each tab 100, 102, 104, 106 includes a corresponding outer edge 108, 110, 112, 114 that extends parallel to axis 66c. A top section 70c of shank 52c is flat, and, thus, the widths of arms 54c, 56c are flat at proximal ends 74c, 76c. The configuration of shank 52c allows anchor 50c to snap onto a wire or wires. Therefore, anchor 50c will be stable during assembly and welding. In some applications, anchor 50c may not require welding.

Each arm 54c, 56c extends from a corresponding end 58c, 60c of shank 52c in an opposite direction relative to axis 66c. Each arm 54c, 56c includes two side edges 55c, 57c. Side edges 55c, 57c intersect at a 40 degree angle ±15 degrees (generally, lower angles for arteries, higher angles for veins and ducts). Side edges 55c, 57c form a sharp point at each corresponding end 62c, 64c.

Arms 54c, 56c include a bend 118 that separates a proximal section 96c and a distal section 94c of each arm 54c, 56c. Both proximal section 96c and distal section 94c diverge away from axis 66c. Proximal section 96c diverges relative to axis 66c at a base angle 119 that lies at the intersection of proximal section 96c and shank 52c and that is, for example, 45 degrees. Bend 118 causes distal section 94c to diverge from axis 66c at a shallower angle than proximal section 96c, for example, 15 degrees. Base angle 119 can range, for example, from 0 degrees to 80 degrees. At bend 118, distal section 94c can form an angle relative to axis 66c that ranges from −20 degrees to 80 degrees.

Though embodiments having different arm configurations are described herein to illustrate the range of embodiments within the scope of the claims, embodiments that have structures similar to sections 94c, 96c and bend 118 may have advantages over other embodiments. Bend 118 of each arm 54c, 56c acts in combination with the corresponding angles at the intersection between shank 52c and each arm 54c, 56c. These angles prevent corresponding distal ends 62c, 64c from engaging the wall of a catheter used to implant a medical device. Proximal section 96c has a steeper slope than distal section 94c relative to axis 66c. Therefore, distal ends 62c, 64c point toward axis 66c when arms 54c, 56c are flattened (e.g., rotated toward axis 66c).

Referring also to FIG. 16, a planar member 68c, which is cut from flat stock material, is used to form anchor 50c (shown in FIGS. 14–15). When member 68c is flat, shank 52c has an "H"-shape (when viewed in the position illustrated in FIG. 16). Anchor 50c is formed in a manner similar to anchor 50b. However, as described above, tabs 100, 102, 104, 108 are curled further about axis 66c to form arcs beyond 180 degrees. Thus, a second forming step, wherein knife edges press two opposing tab pairs 100, 104 and 102, 106 together, is employed. After the first forming step, tab edges 108, 110, 112, 114 are not directly adjacent to wires 42a, 42b. However, tabs 100, 102, 104, 106 can be further curved in the second forming step so that shank 52c better conforms to the shape of wires 42a, 42b.

When fully formed, anchor 50c has an arm span of 0.346"±0.040", and an arm width of 0.0145"±0.001. The outer diameter of the shank is 0.027"±0.0015" in the radial direction. A single arm is 0.114"±0.018" in length. The shank is 0.118"±0.004" in length.

Referring to FIGS. 17–18, anchor 50d includes a shank 52d and two arms 54d, 56d. Shank 52d extends between arms 54d, 56d along a longitudinal axis 66d. Shank 52d has a generally rectangular shape. In contrast to the previously described embodiments, shank 52d is flat and does not curl about axis 66d.

Each arm 54d, 56d extends in an opposite direction relative to axis 66d from a corresponding end 58d, 60d of shank 52d. Each arm 54d, 56d includes two side edges 55d, 57d. Side edges 55d, 57d intersect at a 40 degree angle ±15 degrees, which forms a sharp point at each corresponding end 62d, 64d. Arms 54d, 56d include a bend 118d that joins a proximal section 96d and a distal section 94d of each arm 54d, 56d. Proximal section 96d diverges from shank 52d, for example, at a 40 degree angle ±2 degrees relative to axis 66d. At bend 118d, distal section 94d diverges relative to axis 66d at an angle of 13 degrees ±2 degrees.

Proximal sections 96d include corresponding expanded sections 120 that are directly adjacent to ends 58d, 60d. Expanded sections 120 transition the larger width of shank 52d to the relatively narrower widths of arms 54d, 56d. In addition, expanded sections 120 each include an opening 122 that is directly adjacent to shank 52d. Openings 122 lie along axis 66d.

Anchor 50d is formed from a single planar member that is cut from flat stock. Arms 54d, 56d are bent upwards, and bend 118d is formed at the center of each arm 54d, 56d. Openings 122 are formed in arms 54d, 56d, for example, by electro-discharge machining (EDM). Wires of an implantable medical device, such as wires 42 of filter 32 shown in FIG. 2, extend through openings 122 and along a top side 70d of shank 52d. Wires 42a, 42b parallel axis 66d. A weld secures wires 42a, 42b to shank 52d. Alternatively, shank 52 of anchor 50d could be welded directly to a wire or metallic surface without passing a wire through openings 122.

Figure 19:
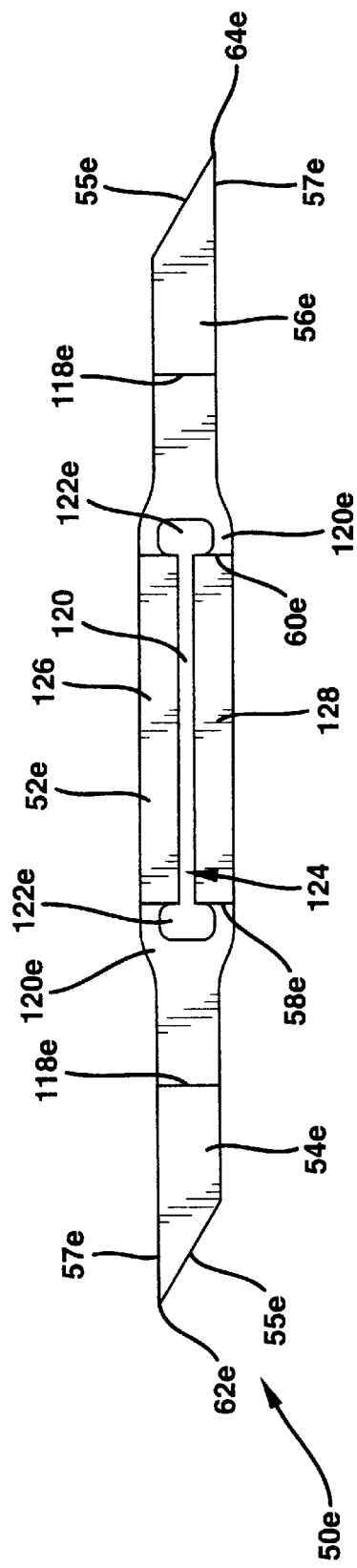
FIG. 19 is a top view of yet another anchor according to the invention.
Figure 20:
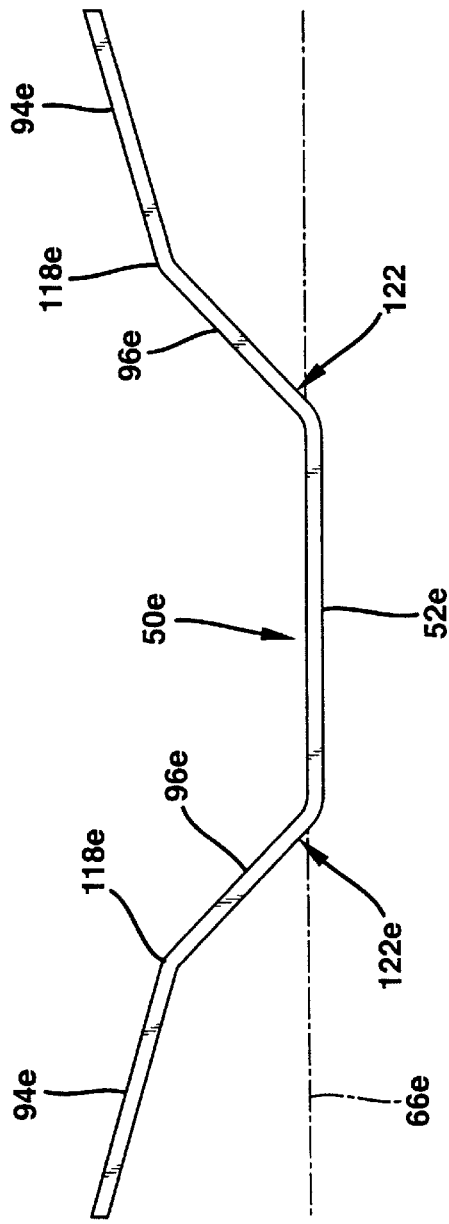
FIG. 20 is a side view of the anchor of FIG. 19.

Referring to FIGS. 19–20, anchor 50e is an embodiment similar in most respects to anchor 50d. However, shank 52e includes a slot 124 that extends longitudinally down the middle of shank 52e between the openings 122. Thus, in effect, openings 122e and slot 124 combine to form a single opening.

Slot 124 allows anchor 50e to be attached to an implantable medical device more easily than anchor 50d. For example, two wires are threaded through the openings 122 of anchor 50d. The same wires would pass transversely one at a time through slot 124, which is narrower than openings 122e and slightly larger than a single wire. Once inserted through slot 124, the wires extend through openings 122e along axis 66e. One wire lies adjacent to the other such that each wire rests against a corresponding solid portion 126, 128 of shank 52e. Wires 42a, 42b lie on either side of the slot. A weld secures wires 42a, 42b to shank 52e.

Figure 21:
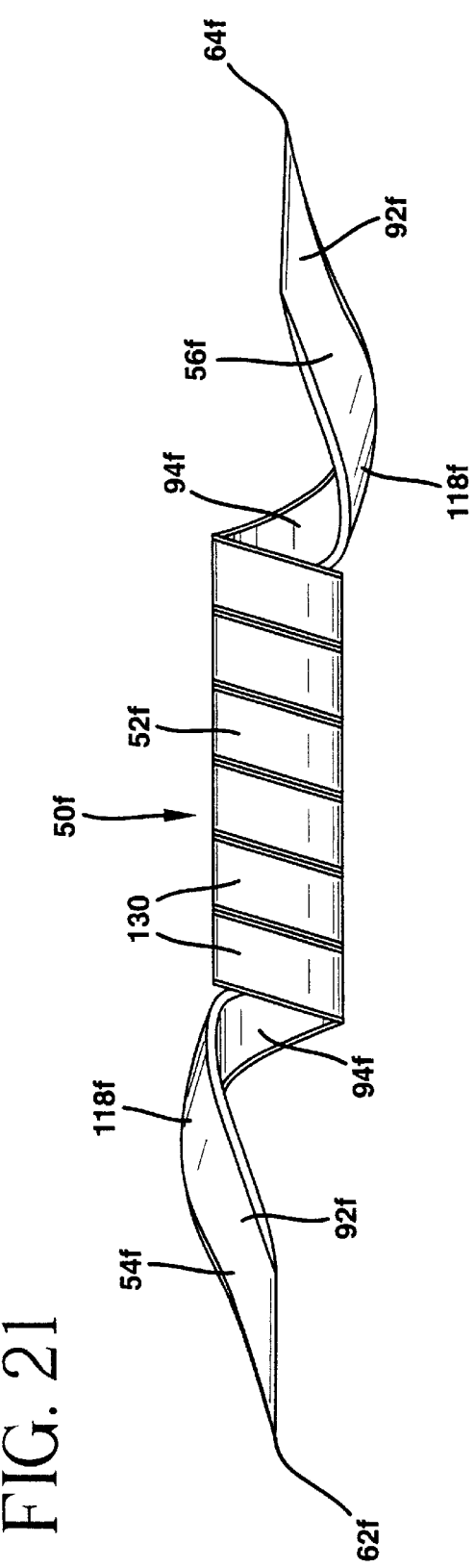
FIG. 21 is a top view of still another anchor according to the invention.
Figure 22:
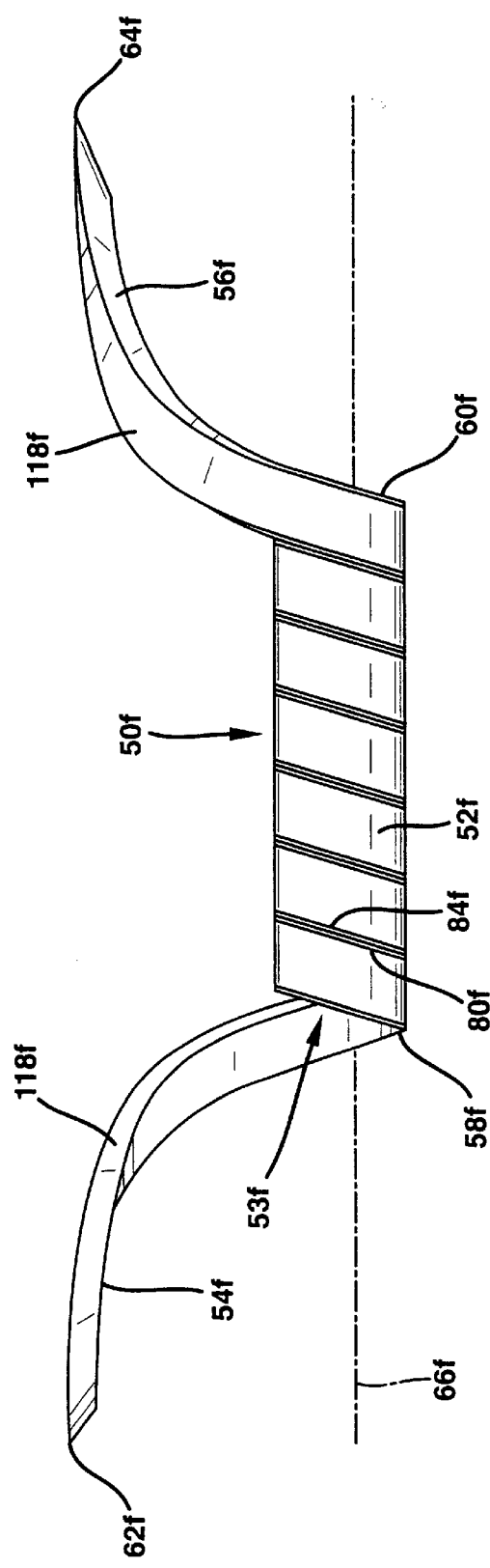
FIG. 22 is a side view of the anchor of FIG. 21.
Figure 23:
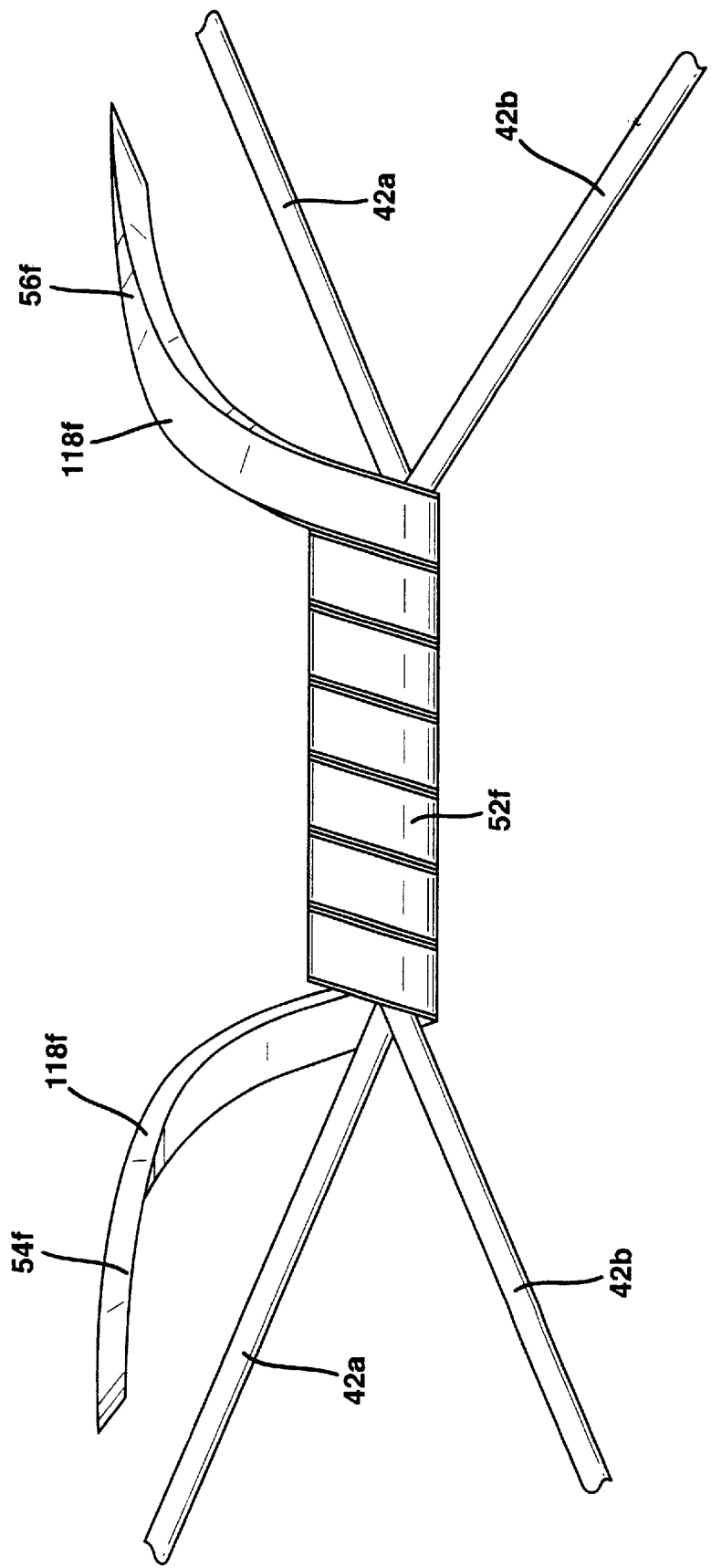
FIG. 23 is a side view of the anchor of FIG. 21 that is attached to a pair of wires of a surgical implant.

Referring to FIGS. 21–23, another embodiment of an anchor 50f includes a shank 52f and two arms 54f, 56f extending from opposite ends 58f, 60f of shank 52f. Shank 52f is curled about axis 66f to form a set of helical loops 130 (six complete loops 130 being shown). Arms 54f, 56f have sharp, pointed distal ends 62f, 64f. Anchor 50f has the same relative appearance when viewed from either end 62f, 64f.

Anchor 50f is formed from a single planar member that is cut from flat stock material. Before anchor 50f is formed, the member is an elongated planar strip. Alternatively, the strip can be a round wire. The strip is curved through a series of helical loops 130 that form a passage 53f. In the illustrated embodiment, an edge 80f of a loop 130 is directly adjacent to, and contacts, an opposite edge 84f of adjacent loop 130. Alternatively, shank 52 could be curled with a greater pitch to leave a gap between edges 80f, 84f. Such a configuration would provide better access to, e.g., wires 42a, 42b during welding.

Arms 54f, 56f curve away from ends 58f, 60f of shank. Each of arms 54f, 56f has a corresponding bend 118f. Each bend 118f is a gradual curve dividing a corresponding arm 54f, 56f into a proximal section 94f and a distal section 92f. Distal section 92f of each arm 54f, 56f extends substantially parallel to axis 66f when compared to proximal section 94f, which is substantially transverse to axis 66f.

Shank 52f attaches to an implantable medical device, such as filter 32 shown in FIG. 2. For example, two wire segments 42a, 42b pass through shank 52f along axis 66f. A weld joins wires 42a, 42b and shank 52f. Arms 54f, 56f extend above wires 42a, 42b on the outer periphery of the medical device.

Figure 24:
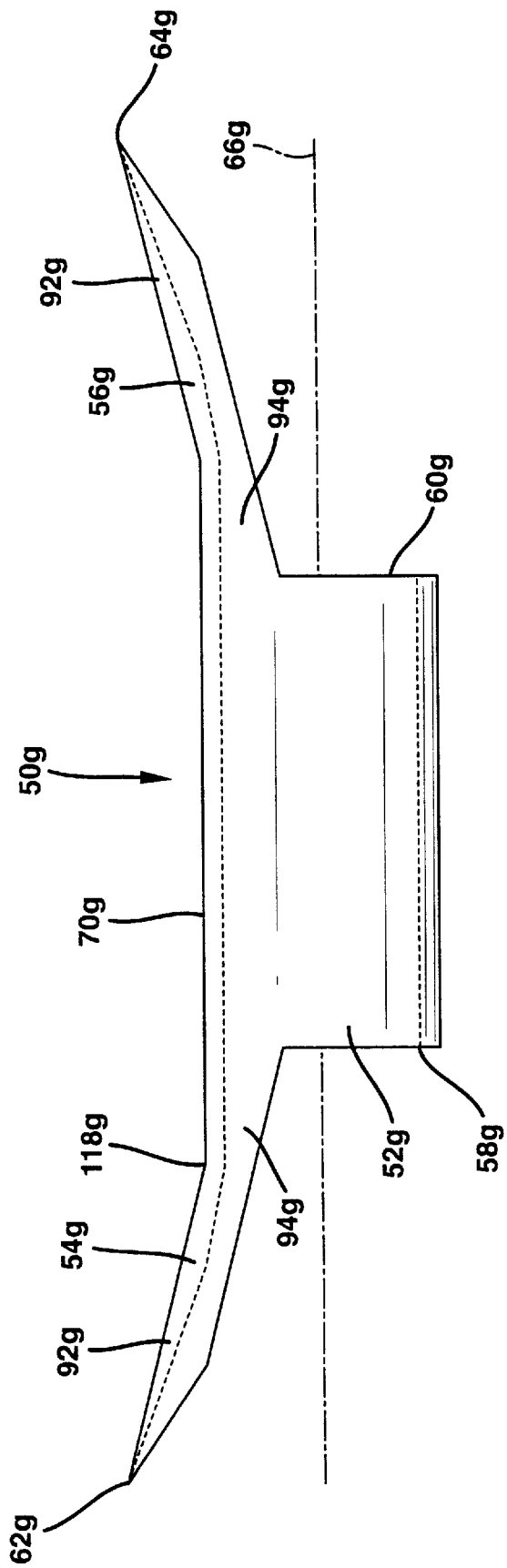
FIG. 24 is a side view of an additional anchor according to the invention.
Figure 25:
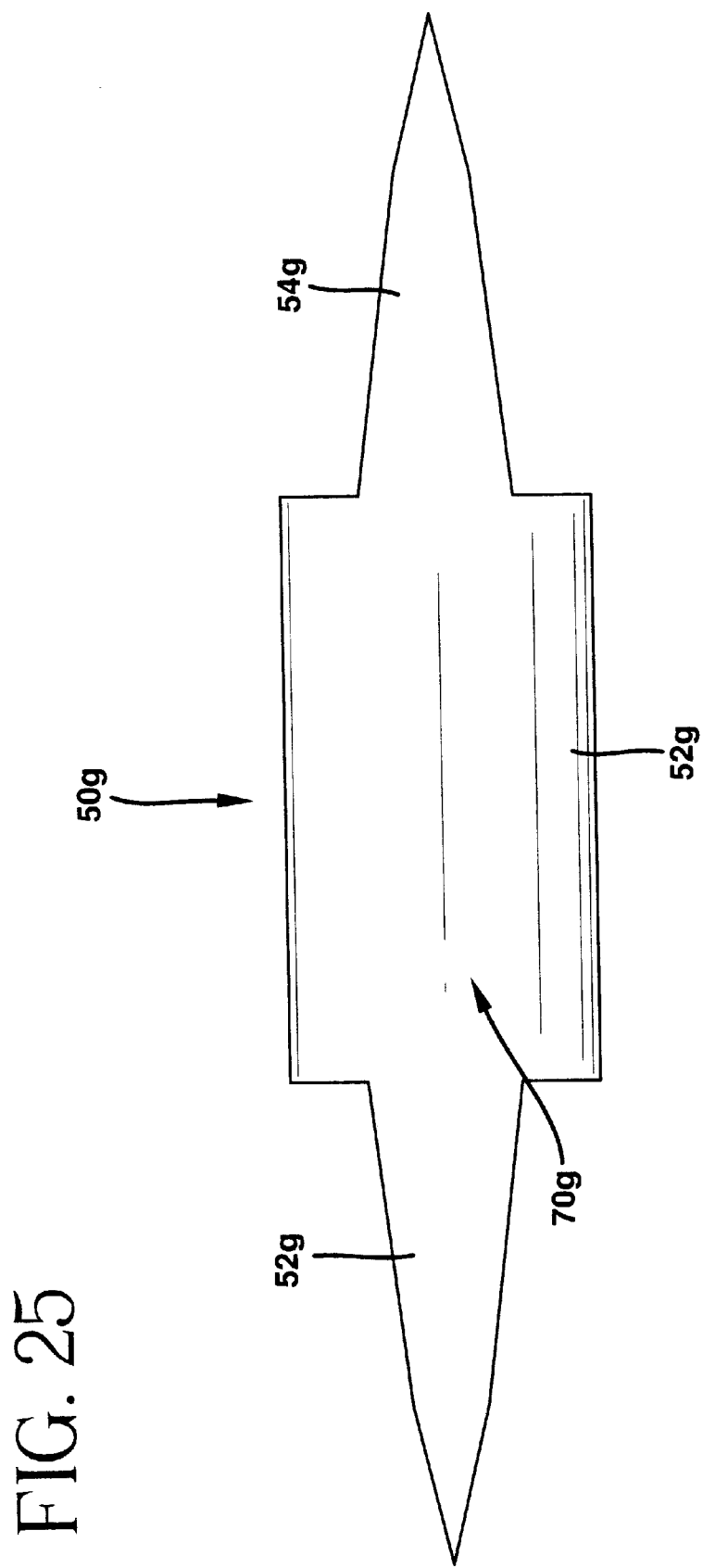
FIG. 25 is a top view of the anchor of FIG. 24.

Referring to FIGS. 24–25, anchor 50g includes a shank 52g and two arms 54g, 56g extending in opposite directions from ends of shank 52g. Shank 52g is a cylindrical tube that forms a cylindrical passage 53g centered on an axis 66g.

Each arm 54g, 56g includes a bend 118g that divides each arm 54g, 56g into proximal and distal sections 94g, 92g. Proximal section 94g parallels axis 66g. Distal section 92g diverges away from axis 66g at an angle. Arms 54g, 56g narrow from respective ends 58g, 60g of shank 52g to corresponding distal ends 62g, 64g of arms 54g, 56g. Distal ends 62g, 64g of arms 54g, 56g form sharp points similar to anchor 50c. However, in contrast to the embodiments previously described, points 62g, 64g are centered relative to the width of corresponding arms 54g, 56g. Anchor 50g has the same relative appearance when viewed from either end 62g, 64g.

A single member forms anchor 50g. For example, anchor 50g can be fabricated from a section of extruded metal tubing by the process of electro-discharge machining (EDM). During manufacture, arms 54g, 56g can be machined in their final positions or arms 54g, 56g can be bent after arms 54g, 56g are machined.

Figure 26:
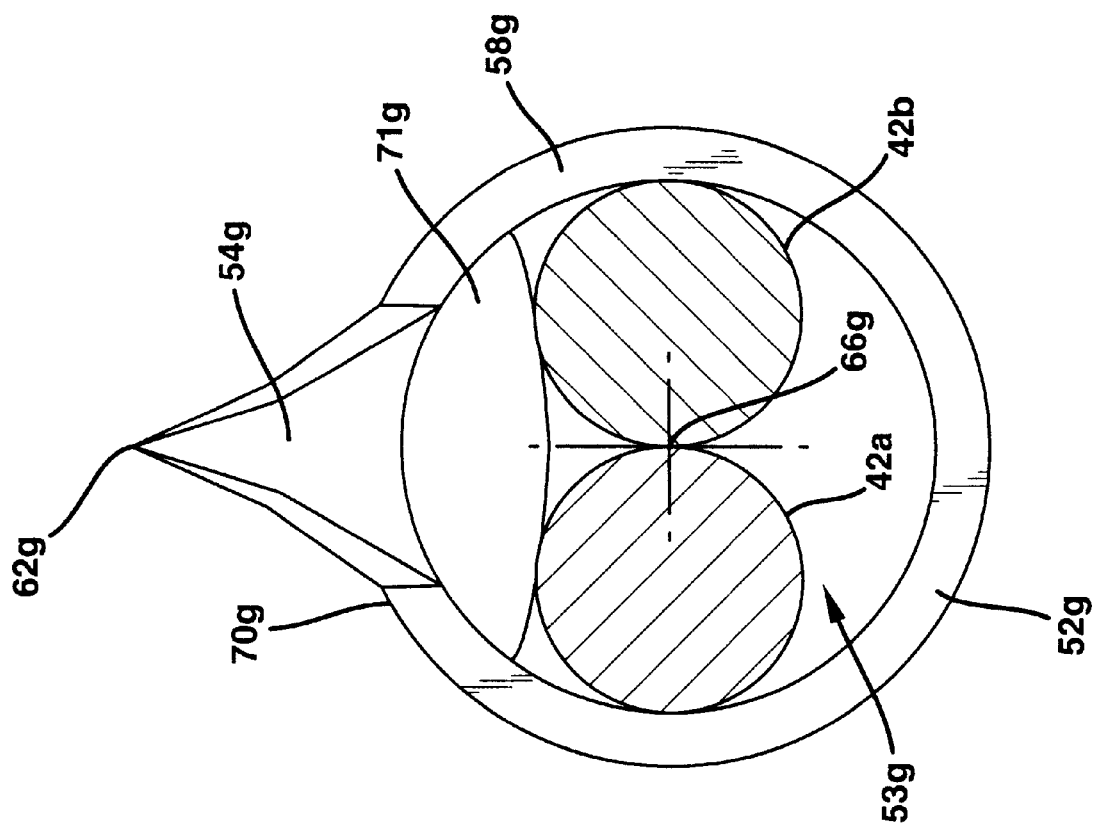
FIG. 26 is an end view of the anchor of FIG. 24 that is attached to two wires of the surgical implant, which are shown in cross-section.

Shank 52g attaches to an implantable medical device. For example, referring to FIG. 26, two wire segments 42a, 42b pass through passage 53g along axis 66g. Alternatively, as with all embodiments described herein, more or fewer wires could pass through shank 52g. A weld, which is located on a top section 70g, joins wires 42a, 42b and shank 52g. When resistance welded, a portion of top section 70g is pressed downward until an inner wall portion 71g of shank 52g contacts wires 42a, 42b. Once anchor 50g is attached to the medical device, arms 54g, 56g extend above wires 42a, 42b on the outer periphery of the medical device, for example, blood clot filter 32. When compared to the open embodiments previously described, shank 52g is more difficult to weld because the closed hypotube restricts penetration to wires 42a, 42b. Alternatively, windows could be cut in shank 52g to increase penetration of the weld.

Figure 27:
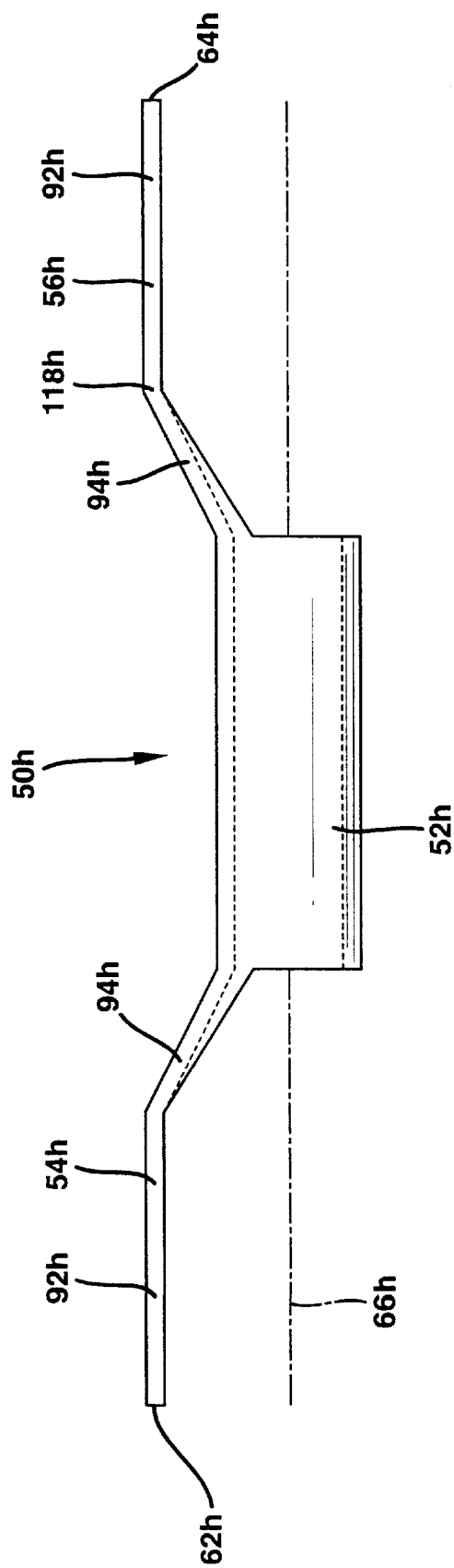
FIG. 27 is a side view of another anchor according to the invention.
Figure 28:
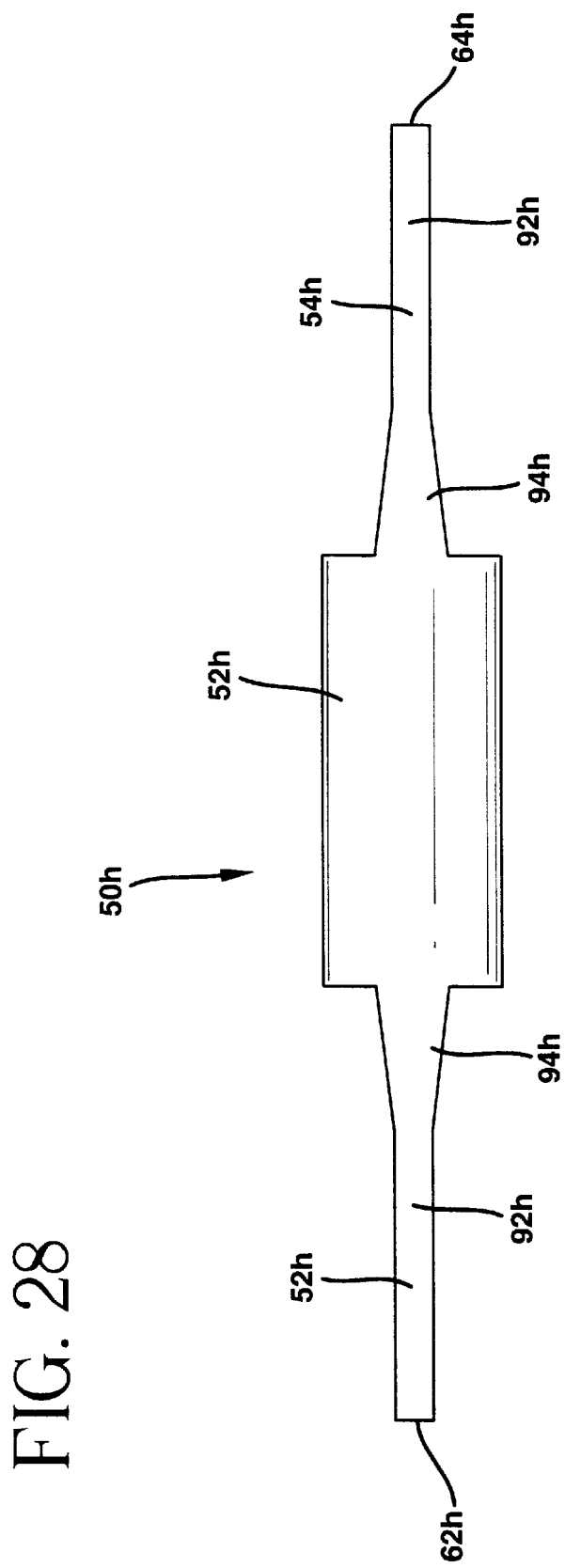
FIG. 28 is a top view of the anchor of FIG. 27.
Figure 29:
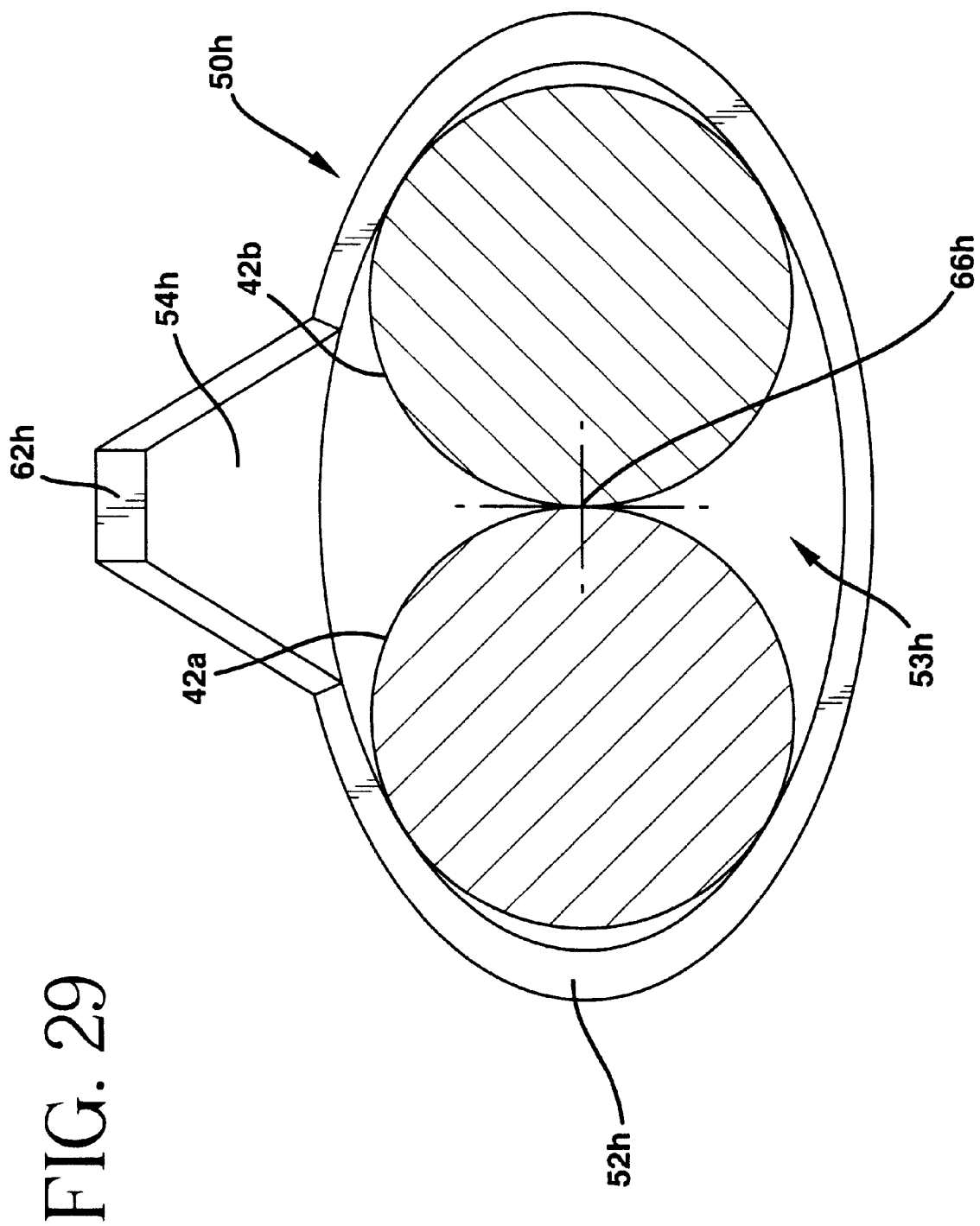
FIG. 29 is an end view of the anchor of FIG. 27 that is attached to two wires of the surgical implant, which are shown in cross-section.

Referring to FIGS. 27–29, yet another embodiment of an anchor 50h has a tubular shank 52h that is similar to shank 52g of anchor 50g. However, anchor 50h includes several structural differences from anchor 50g. First, passage 53h of shank 52h is elliptical. The elliptical shape allows shank 52h to have a lower profile in the radial direction, i.e., the direction extending transversely from the longitudinal axis, than cylindrical shank 52g, when attached to an implantable medical device. However, an elliptical configuration, especially when forming anchors by reshaping a cylindrical tube constructed of nitinol, can result in cracking of shank 52g. Thus, shank 52g may preferably be formed by extrusion.

Second, arms 54h, 56h have flat distal ends 62h, 64h, and a distal section 92h of each arm 54h, 56h extends parallel to axis 66h while a proximal section 94h diverges from axis 66h. Therefore, arms 54h, 56h do not tend to pierce or puncture wall 22 of lumen 10, shown in FIG. 1. The friction between wall 22 and distal sections 92h secures the implantable medical device. An implantable medical device may distend a lumen to produce the friction between the wall of the lumen and anchor 50h. For example, a surgical stent generally will provide outward radial support for a damaged blood vessel. However, a blood clot filter, which is placed in a healthy blood vessel, generally will be selected to produce little or no distension of the blood vessel.

Figure 30:
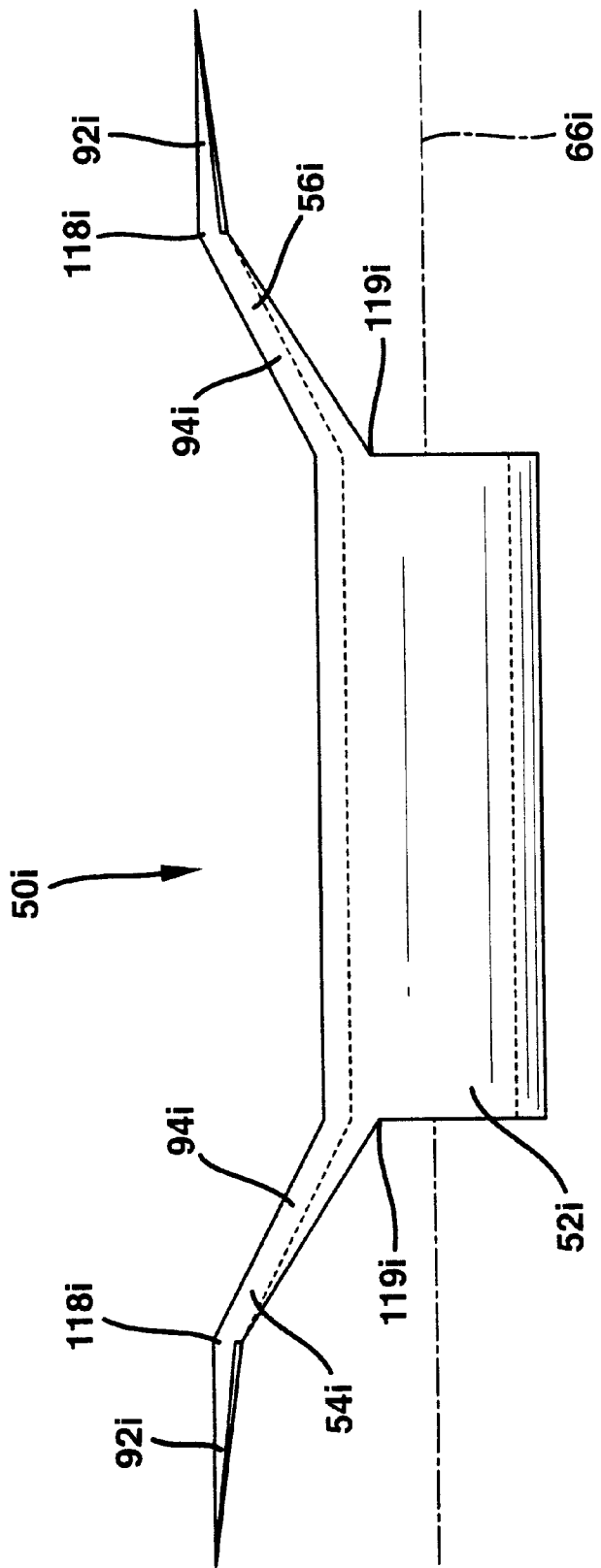
FIG. 30 is a side view of yet another anchor according to the invention.
Figure 31:
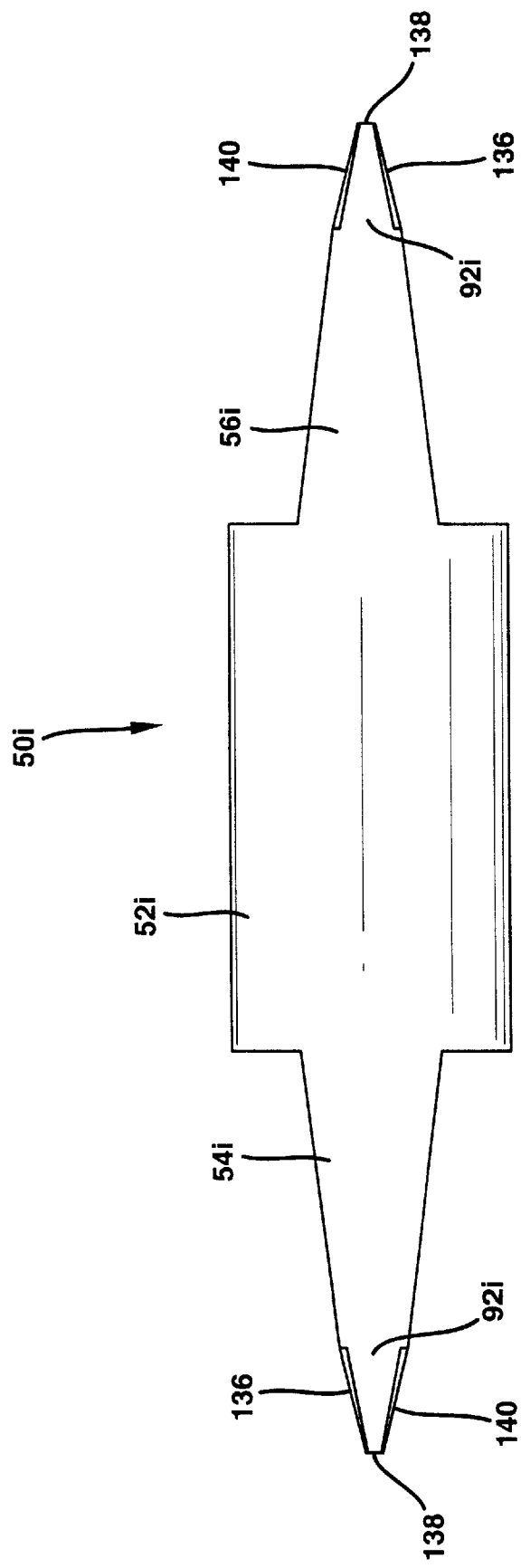
FIG. 31 is a top view of the anchor of FIG. 30.
Figure 32:
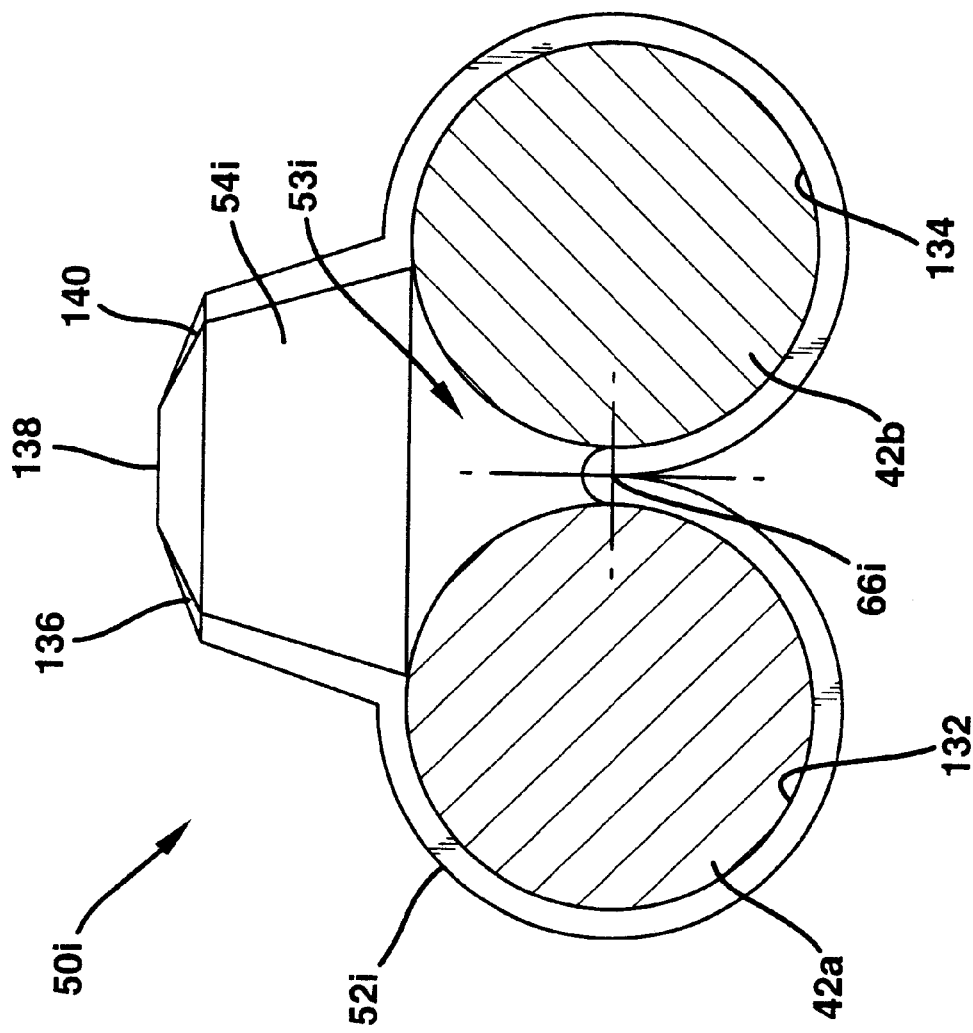
FIG. 32 is an end view of the anchor of FIG. 30 that is attached to two wires of the surgical implant, which are shown in cross-section.

Referring to FIGS. 30–32, anchor 50i also has a tubular shank 52i. However, anchor 50i also has several features not included in either anchor 50g or anchor 50h. First, passage 53i of shank 52i includes two lobes 132, 134 that extend along axis 66i. Thus, shank 52i fits even closer to wires 42a, 42b than elliptical shank 52h, and, when attached to an implantable medical device, shank 52i provides an even lower radial profile than either cylindrical shank 52g or elliptical shank 52h.

Second, each end 62i, 64i of corresponding arms 54i, 56i is bounded by sharp edges 136, 138, and 140 on three sides. Two edges 136, 140 extend along the sides of each arm 54i, 56i, and one edge 138 extends transversely between the side edges 136, 140 at the tip of each arm 54i, 56i. Thus, although distal sections 92i extend parallel to axis 66i rather than diverging from axis 66i, ends 62i, 64i will pierce the wall of a lumen. For most applications, embodiments within the scope of the invention having sharp edges, for example, three sharp edges similar to edges 136, 138, and 140 or two sharp edges converging at a point, may be preferable to other embodiments lacking a sharp edge.

Generally, grind angles of the sharp edges can be formed by grinding one side of the edge for most applications within the body. However, to improve the ability of the anchor to move relative to a delivery device during implantation without engaging, e.g., the inner-wall of a catheter of the delivery device, it may be preferable to grind opposing sides of the same edge to form a "wedge-shaped" sharp edge. (An example of a delivery device is described below in conjunction with FIG. 34.)

Figure 33:
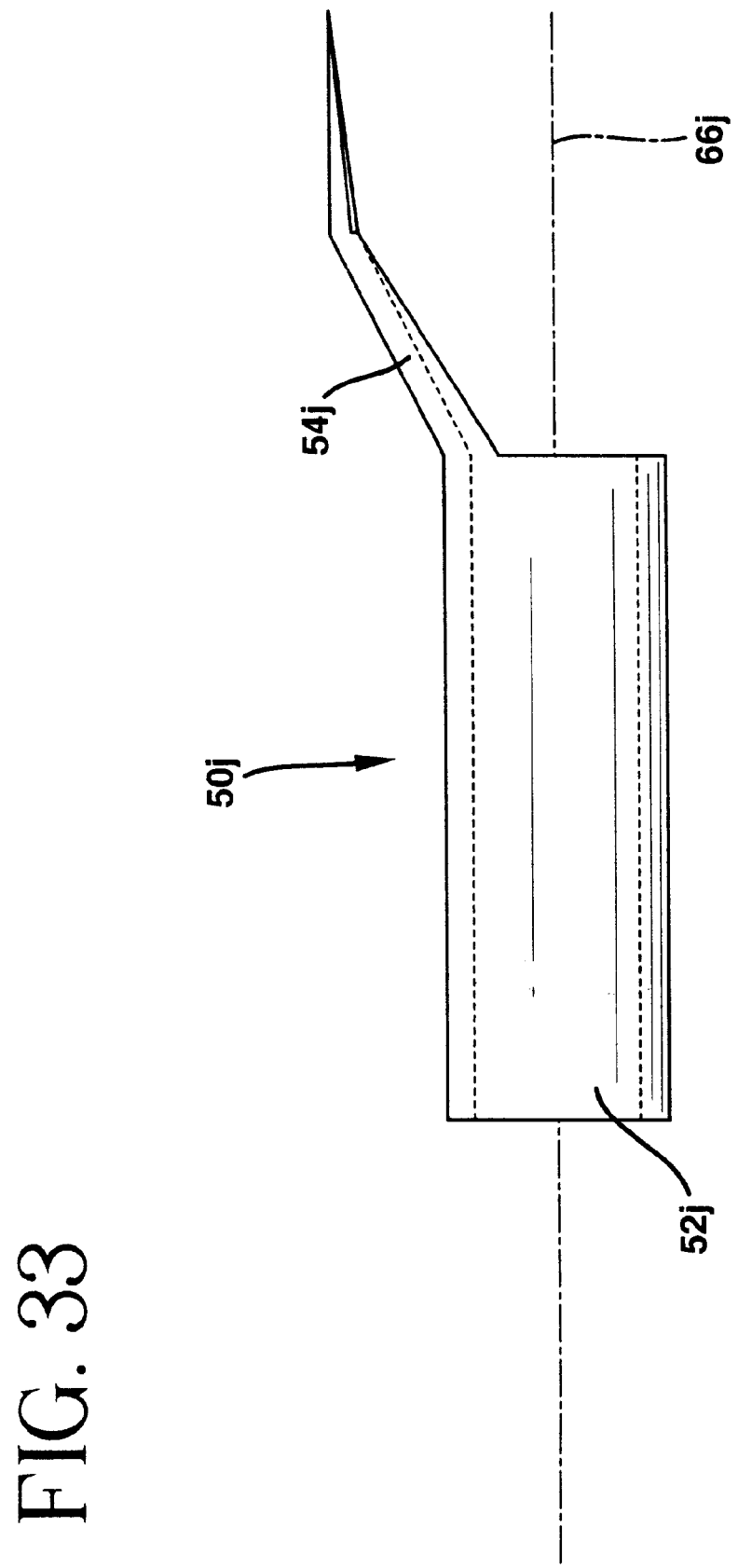
FIG. 33 is a side view of an anchor according to the invention having only one arm.

Referring to FIG. 33, another embodiment of an anchor 50j has only one arm 54j attached to a shank 52j. In all other respects, anchor 50j is similar to anchor 50i. Similarly, all anchors described herein could be configured with one arm rather than two arms. Such anchors may minimize trauma and facilitate removal of the implantable medical device. Typically, when attached to an implantable medical device, most anchors 50j are oriented to oppose the force of blood flow through the filter. However, some anchors 50j could be oriented to oppose motion of the filter opposite the direction of blood flow, for example, forces exerted by the blood vessel. Also, an anchor according to the invention may have more than two arms.

An implantable medical device that includes anchors according to the invention is inserted in a manner similar to implantable medical devices that include prior art anchors. For example, shank 52i of anchor 50i, shown in FIGS. 30–32, is attached to an implantable medical device, such as filter 32 shown in FIG. 2. Subsequently, filter 32 is radially compressed about the longitudinal axis. When compressed, anchor 50i has a small radial profile. The small profile results from one or more factors. For example, anchor 50i is a single, integrally formed piece of material; arms 54i, 56i are flexible and flatten against filter 32 when compressed; and shank 52i is lobed and, thus, reduces the radial profile when compared to circular shanks such as 52g shown in FIG. 26.

Because wire mesh 34 of filter 32 is thin, the size of the anchors may limit the maximum compression of filter 32 when anchors are attached. Thus, the anchors may limit the application of filter 32 to relatively larger blood vessels. However, because anchors according to the invention, such as anchors 50i, have features that reduce the overall radial profile of the compressed device, a physician can insert filter 32 into relatively smaller blood vessels. Also, a relatively small anchor profile reduces the strain on the medical device when compressed.

Figure 34:
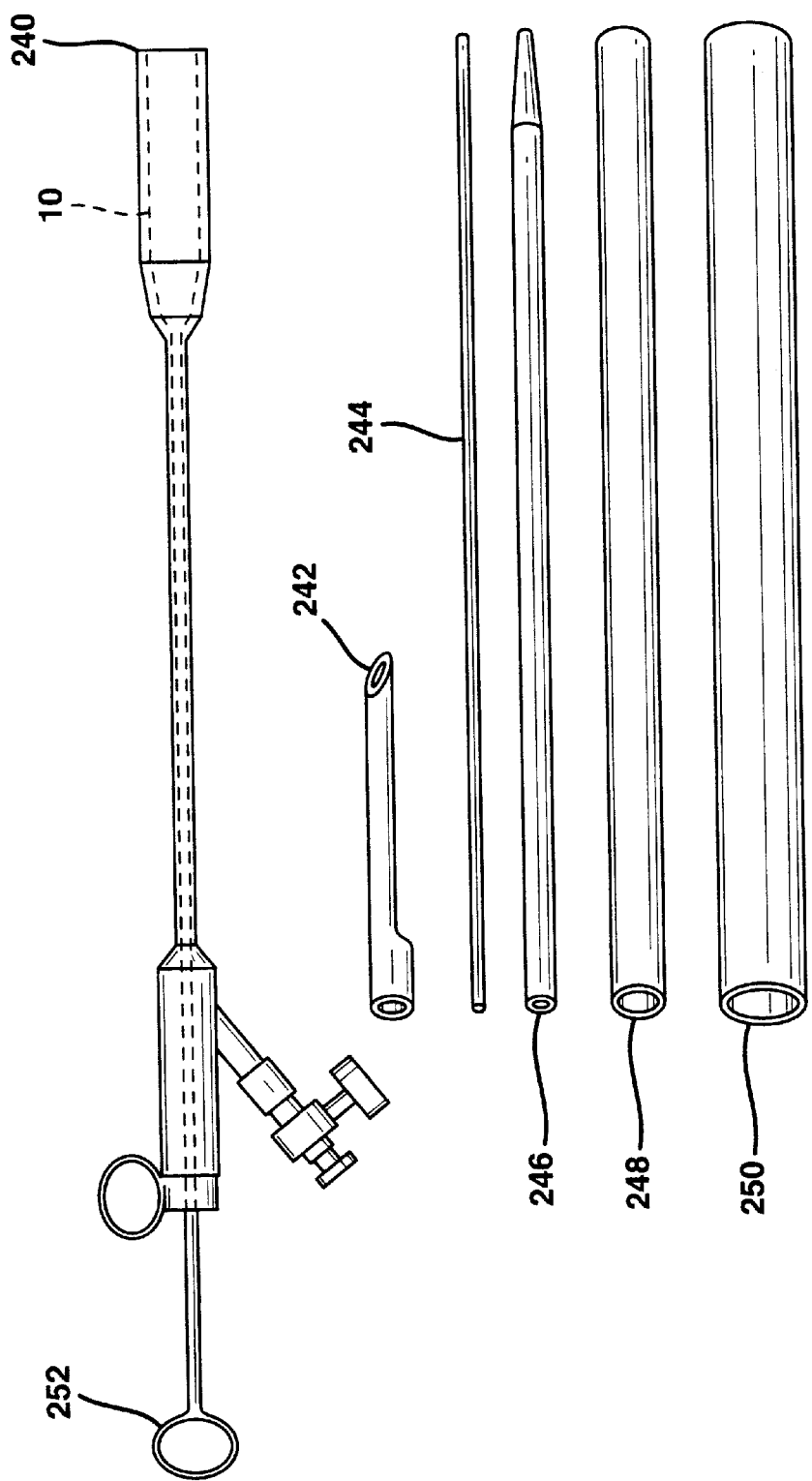
FIG. 34 is a schematic view of a device used to insert a blood filter into a lumen using an anchor according to the invention.
Figure 35:
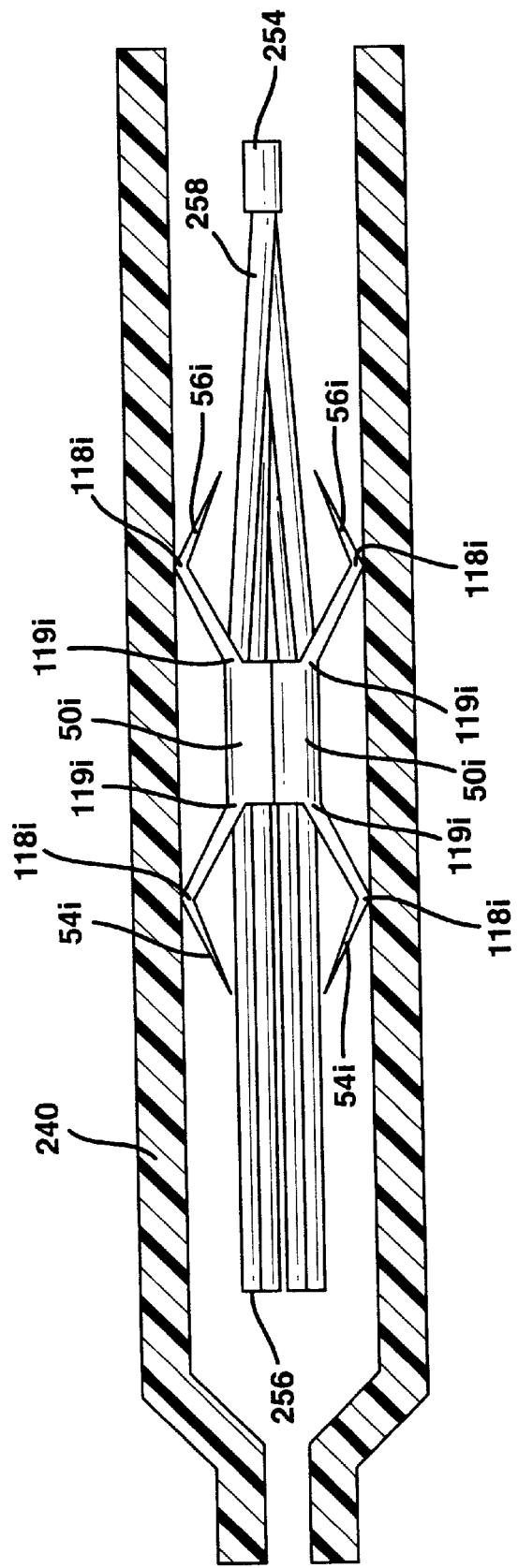
FIG. 35 is a schematic view of the anchor of FIG. 30 inserted into a cartridge of the device of FIG. 34, wherein arms of the anchor are rotated toward a central axis of the cartridge.

Referring to FIGS. 34 and 35, the physician radially compresses an implantable medical filter device 254 and inserts the device into a cartridge 240. The physician punctures a lumen, such as a vein, with a needle 242 and inserts a guide-wire 244 into the vein through the puncture hole. The physician then inserts a small gauge catheter 246 into the vein over guide-wire 244. Next, the physician slides a larger catheter 248 over catheter 246 to dilate lumen 12 and the surrounding tissue. The physician then places a sheath 250 over catheters 246, 248 and removes catheters 246, 248 and guide-wire 244. The physician slides cartridge 240 relative to sheath 250, and pulls sheath 250 to deploy device 254. While deploying, a rod 252 holds device 254 in a stationary position relative to the wall of lumen 12 to ensure accurate placement of device 254, and sheath 250 is pulled back to expose device 254. A conical portion 258 of device 254 is exposed by cartridge 240 before a cylindrical portion 256 of device 254.

Implantable filter device 254 includes two anchors 50i. All four arms 54i, 56i of anchors 50i are compressed by rotating the arms inward toward the center of the cylindrical cartridge. Each arm 54i, 56i includes a bend 118i and a base angle 119i that direct the sharp edges and points of anchor 50i away from the inner wall of cartridge 240, which is typically made of a plastic material that can be caught or snagged by a sharp edge or point. Therefore, anchors 50i can move relative to cartridge 240 without inadvertently piercing or snagging the inner wall of cartridge 240.

Arms 54i, 56i of anchors 50i may have the smallest amount of flexibility when compared to the arms of other anchors disclosed herein. Other anchors having more flexible configurations relative to anchor 50i may provide even lower profiles when inserted into cartridge 240. Note also that the profile of implantable filter device 254 can be further reduced by placing anchors 50i in a staggered position.

When deployed, device 254 expands radially within the vein. For example, if device 254 is constructed of shape memory material (or any other material that can be compressed without permanent deformation), device 254 will tend to return to the shape prior to compression. Thus, cylindrical portion 256 of device 254 exerts a radial force that drives anchors 50i against the wall of the vein. Due to the configuration of arms 54i, 56i, anchor 50i will pierce the wall of the vein. If a different anchor is employed having a configuration such as arms 54h, 56h, shown in FIG. 27–29, the arms may secure device 254 by frictional forces caused by pressing against the wall of the vein without puncturing the wall.

Figure 36:
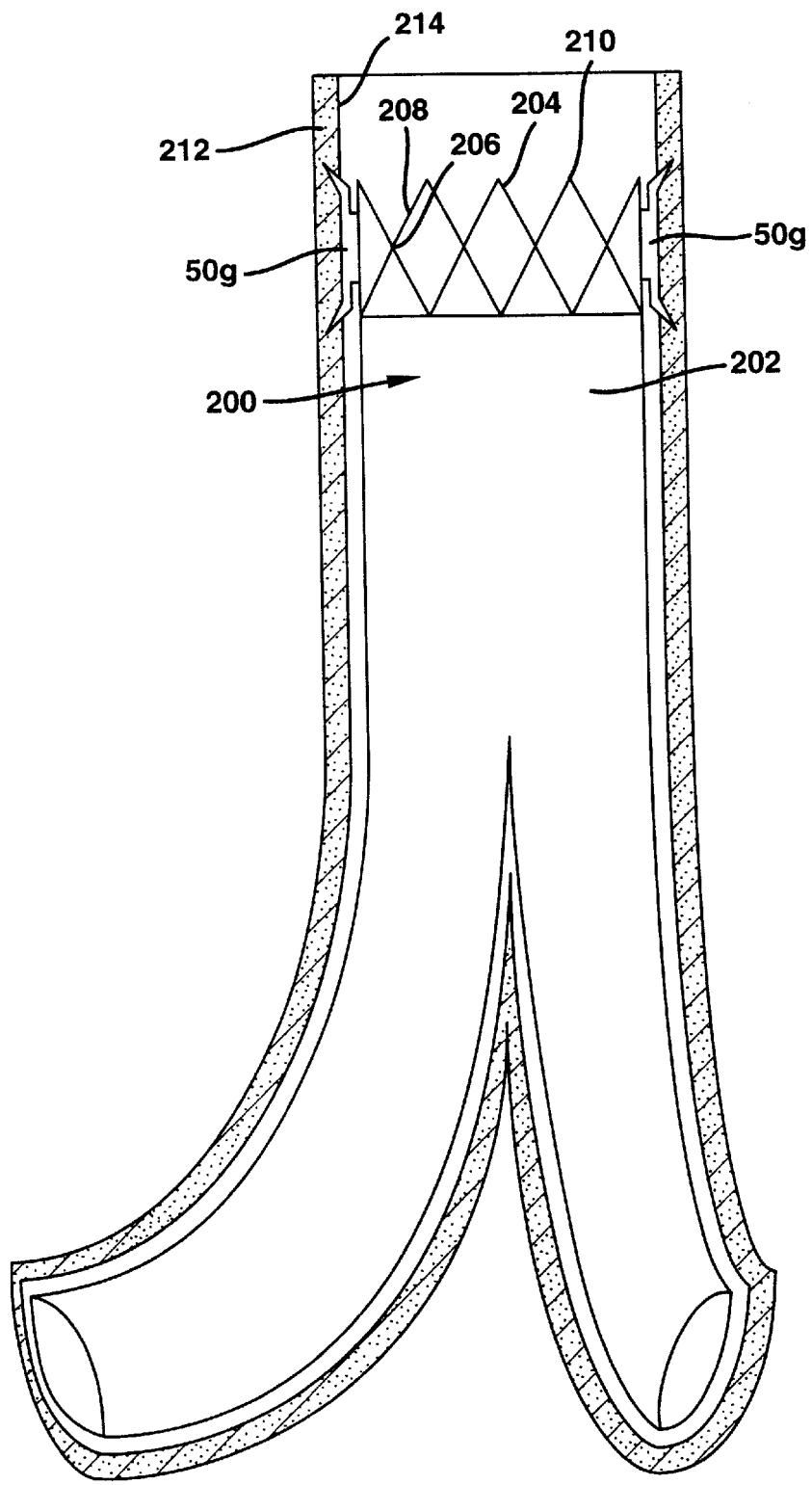
FIG. 36 is a diagrammatic view in partial section of a surgical graft secured by anchors according to the invention.

The anchors according to the invention can secure implantable medical devices other than blood clot filters. For example, referring to FIG. 36, anchor 50g attaches to a surgical graft 200. Surgical graft 200 includes a sheath 202 that surrounds a wire mesh section 204. Sheath 202 is fabricated from a low porosity material, for example, Dacron® or Teflon®, and wire mesh section 204 is constructed of a metallic material, such as titanium. Anchors 50g attach to graft 200 at corresponding junctures 206 of two wire strands 208. Anchors 50g attach to a portion of wire mesh section 204 that extends beyond an end 210 of sheath 208. Graft 200 is compressed radially and inserted into a damaged blood vessel 212. Anchors 50g engage a wall 214 of the vessel when graft 200 expands within damaged blood vessel 212.

Figure 37:
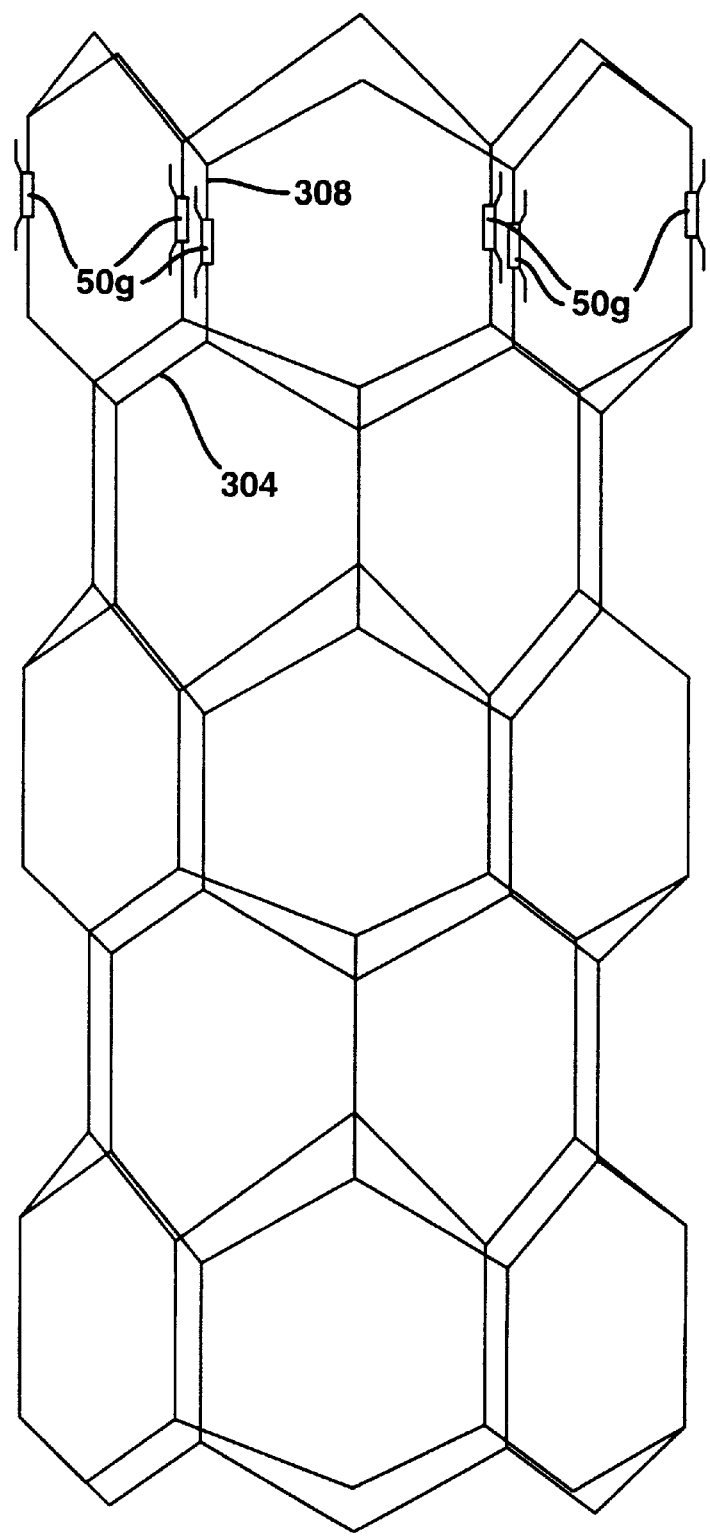
FIG. 37 is a schematic view of surgical stent including anchors according to the invention.

Referring to FIG. 37, anchor 50g attaches to a surgical stent 300. Surgical stent 300 includes a wire mesh section 304 that supports the wall of a damaged blood vessel. Wire mesh section 304 can be constructed of a metallic material such as titanium. Anchors 30g attach to surgical stent 300 along wire strands 308 located near an end 310 of stent 300. Stent 300 is compressed radially and inserted into a damaged blood vessel. Anchors 30g engage the wall of the vessel when stent 300 expands within the damaged blood vessel.

As described herein, embodiments within the scope of the claims can attach to implantable medical devices that have wire mesh sections, such as filters, grafts, and stents. Embodiments within the scope of the claims also can attach to other types of implantable medical devices. For example, embodiments within the scope of the claims can be attached to implantable medical devices along portions other than wire strands or similar attachment means. Embodiments within the scope of the claims may attach to a biocompatible material, such as kevlar, by piercing the material and securing the anchor in a manner similar to a staple. Embodiments within the scope of the claims may be sutured to an implantable medical device along openings in the shank that accommodate the sutures, or sutures may wrap around the shank to attach the anchor to the implantable device. An anchor, such as 50f or 50g, may attach to a plastic section of an implantable medical device without a weld that could degrade the plastic section. In addition, an anchor, which is not welded or otherwise secured along a wire, could slide along the axis relative to the implantable medical device. An anchor could be attached to the medical device, for example, by gluing, swaging, high frequency vibration welding, or injection molding.

Also, embodiments within the scope of the claims could attach to types of implantable medical devices other than those described herein. For example, in addition to filters, stents and grafts, embodiments within the scope of the claims could attach to valves, packing leads, tethered devices that are removable, infusion devices, and other types of stents such as larger stents used in the gastrointestinal tract. Embodiments within the scope of the claims could be attached to expandable devices, such as balloon expandable stents. Embodiments within the scope of the claims could be attached to devices designed to be permanently incorporated into the body. For example, such embodiments could have relatively weaker attachments suitable to maintain the device in position until the body tissue grows around the device to secure it, for example, 60 days.

The material that forms anchors within the scope of the claims may be chosen based on the application of the particular anchor. For example, the material may match the base material of the implantable medical device to prevent corrosion; the material may be radiopaque to facilitate medical tests and provide better visualization under fluoroscopy or other applications; the material may be malleable to enhance formability such as with stainless steel; or the material may be a shape memory material or a resilient material to enhance the flexibility or recovery of the anchor.

Other embodiments are within the scope of the claims. The term medical device includes devices that are anchored using both surgical techniques and non-surgical techniques. In addition, different features of the embodiments described in the specification can be combined to configure additional embodiments. For example, aspects of different embodiments of the invention could be combined to reduce the overall profile of the implantable medical device when the device is compressed prior to insertion in the body. In typical applications, the anchor will limit the minimum profile of the compressed device. Thus, the lower the profile of the individual anchors, the lower the overall profile of the compressed implantable device.

The embodiments described herein, including all dimensions, materials, structures, arrangements, combinations, and methods are provided as examples. It is evident that those skilled in the art may now make numerous modifications to and uses of and departures from the specific apparatus and techniques disclosed herein without departing from the inventive concepts. Consequently, the invention is to be construed as embracing each and every novel feature and novel combination of features present in or possessed by the apparatus and techniques disclosed herein and limited only by the spirit and scope of the appended claims.

What is claimed is:

1. An anchor adapted to secure an implantable device within a body by engaging a wall of the body, the anchor comprising:

a shank and a first arm extending from a proximal end attached to the shank to a distal end, wherein the shank and the first arm are integrally formed from a single member, wherein the shank is attachable to the device upon placement thereon, and the first arm is adapted for engaging the wall of the body when the device is implanted within a body.

2. The anchor of claim 1, wherein the first arm extends from an end of the shank.

3. The anchor of claim 1, wherein the anchor is formed from flat stock.

4. The anchor of claim 1, further comprising a second arm having a proximal end attached to the shank, wherein the second arm is also integrally formed from the single member.

5. The anchor of claim 4, wherein the first arm and the second arm are oriented in opposing directions along an axis.

6. The anchor of claim 5, wherein the proximal ends of the first and second arms extend from opposite ends of the shank.

7. The anchor of claim 5, wherein the shank comprises an elongated section disposed at an angle to both the first arm and the second arm, a length of the shank being curled about the axis to form a loop.

8. The anchor of claim 5, wherein the shank comprises an elongated section curled about the axis to form a plurality of loops.

9. The anchor of claim 5, wherein the shank is curled about the axis, one edge of the shank being adjacent to an opposite edge of the shank.

10. The anchor of claim 5, wherein the shank is curled about the axis, one edge of the shank being oriented in substantially the same direction as an opposite edge of the shank.

11. The anchor of claim 5, wherein the shank further comprises a first tab section extending from one edge of the shank and a second tab section extending from an opposite edge of the shank, the tab sections being curled about the axis.

12. The anchor of claim 5, wherein the shank extends along the axis at an angle to both the first and second arms, the proximal end of each arm defining respective openings, the openings being aligned along the axis.

13. The anchor of claim 12, wherein the shank defines a slot that extends between and connects the openings.

14. The anchor of claim 5, wherein the shank comprises a tube.

15. The anchor of claim 14, wherein the tube has a cylindrical shape.

16. The anchor of claim 14, wherein the tube has an elliptical shape.

17. The anchor of claim 14, wherein the tube further defines a hollow parallel to the axis.

18. The anchor of claim 14, wherein the hollow of the tube has at least two lobes.

19. The anchor of claim 5, wherein the arms extend at an angle relative to the axis.

20. The anchor of claim 1, wherein the arm is curved.

21. The anchor of claim 1, wherein the arm includes a first bend between the proximal end and a distal end of the arm.

22. The anchor of claim 21, wherein the arm includes a second bend between the first bend and the distal end of the arm.

23. The anchor of claim 1, further comprising:
   a first portion of the arm between a proximal end of the arm and a bend in the arm, the first portion having a first slope relative to the axis;
   a second portion of the arm between the bend and a distal end of the arm, the second portion having a second slope relative to the axis; and
   wherein the first slope is steeper than the second slope.

24. The anchor of claim 1, wherein the arm further comprises a pointed distal end.

25. The anchor of claim 1, wherein the arm further comprises a rounded distal end.

26. The anchor of claim 1, wherein the arm further comprises a sharp edge.

27. The anchor of claim 1, wherein the arm further comprises a dull edge.

28. The anchor of claim 1, wherein the member comprises shape-memory material.

29. The anchor of claim 1, wherein the member comprises stainless steel.

30. The anchor of claim 1, wherein the member comprises titanium.

31. The anchor of claim 1, wherein the member comprises a radiopaque material.

32. The anchor of claim 1, in combination with the implantable device wherein the shank of the anchor is secured to the implantable device.

33. The combination of claim 32, wherein the shank is secured to a wire of the implantable device.

34. The combination of claim 32, wherein the implantable device comprises a filter.

35. The combination of claim 32, wherein the implantable device comprises a stent.

36. The combination of claim 32, wherein the implantable device comprises a graft.

37. The combination of claim 32, wherein the shank of the anchor is secured to the implantable device by an adhesive means.

38. An implantable device having an anchor, the anchor comprising: a single member having a first arm, a second arm, and a shank attached to the first arm and the second arm, wherein the first arm, the second arm, and the shank are integral sections of the member, and the shank is attachable to the device upon placement thereon.

39. The device of claim 38, wherein the first and second arms are flexible.

40. The device of claim 38 wherein said shank of the anchor is secured to the device by an adhesive means.

41. A method of forming an implantable medical device including an anchor for securing said device in a body comprising the steps of:
   (a) forming flat stock into said anchor having a shank section and an arm section;
   (b) bending said shank section about an axis;
   (c) attaching said shank section to said implantable device upon placement thereon; and
   (d) securing said shank section to said device.

42. The method of claim 41 wherein the securing of said shank section to said device is by an adhesive means.

43. The method of claim 41 further comprising the step of configuring said arm section.

44. The method of claim 43 wherein the step of configuring said arm section further comprises shaping, angling, curving, bending, twisting, sharpening, or dulling the arm.

45. A method of forming an implantable medical device including an anchor for securing said device in a body comprising the steps of:
   (a) forming flat stock into said anchor having a shank section and an arm section;
   (b) providing a hollow within said shank section that extends along an axis;
   (c) attaching said shank section to said implantable device upon placement thereon; and
   (d) securing said shank section to said device.

46. The method of 45 further comprising the step of configuring said arm section.

47. The method of claim 46 wherein the step of configuring said arm section further comprises shaping, angling, curving, bending, twisting, sharpening, or dulling the arm.

* * * * *